US009107866B2

(12) United States Patent
Savarino et al.

(10) Patent No.: US 9,107,866 B2
(45) Date of Patent: *Aug. 18, 2015

(54) **ADHESIN-ENTEROTOXIN CHIMERA BASED IMMUNONGENIC COMPOSITION AGAINST ENTEROTOXIGENIC *ESCHERICHIA COLI***

(75) Inventors: Stephen J Savarino, Kensington, MD (US); Randall K Holmes, Golden, CO (US); Michael G Jobling, Aurora, CO (US)

(73) Assignees: The United States of America As Represented by the Secretary of the Navy, Washington, DC (US); The Regents Of The University Of Colorado, A Body Corporate, Denver, CO (US)

( * ) Notice: Subject to any disclaimer, the term of this patent is extended or adjusted under 35 U.S.C. 154(b) by 1313 days.

This patent is subject to a terminal disclaimer.

(21) Appl. No.: 11/988,598

(22) PCT Filed: Jan. 11, 2007

(86) PCT No.: PCT/US2007/000712
§ 371 (c)(1),
(2), (4) Date: Jan. 10, 2008

(87) PCT Pub. No.: WO2007/114878
PCT Pub. Date: Oct. 11, 2007

(65) Prior Publication Data
US 2009/0136567 A1    May 28, 2009

Related U.S. Application Data

(60) Provisional application No. 60/758,099, filed on Jan. 11, 2006.

(51) Int. Cl.
*A61K 39/02* (2006.01)
*A61K 39/108* (2006.01)
*A61K 39/00* (2006.01)

(52) U.S. Cl.
CPC ....... *A61K 39/0258* (2013.01); *A61K 2039/522* (2013.01); *A61K 2039/523* (2013.01); *A61K 2039/54* (2013.01); *A61K 2039/543* (2013.01); *A61K 2039/545* (2013.01); *A61K 2039/6037* (2013.01); *A61K 2039/627* (2013.01)

(58) Field of Classification Search
None
See application file for complete search history.

(56) References Cited

U.S. PATENT DOCUMENTS

| 5,698,416 | A | 12/1997 | Wolf et al. |
| 6,902,736 | B2 | 6/2005 | Altboum et al. |
| 2002/0086037 | A1 | 7/2002 | Hultgren et al. |
| 2002/0150587 | A1 | 10/2002 | Langemann et al. |
| 2003/0021803 | A1* | 1/2003 | Langridge et al. ......... 424/190.1 |
| 2003/0099665 | A1 | 5/2003 | Langemann et al. |
| 2003/0138449 | A1 | 7/2003 | Langemann et al. |
| 2003/0199071 | A1 | 10/2003 | Langemann et al. |
| 2005/0054075 | A1 | 3/2005 | Turner et al. |
| 2005/0136070 | A1 | 6/2005 | Altboum et al. |
| 2005/0241024 | A1 | 10/2005 | Langridge et al. |
| 2006/0153878 | A1 | 7/2006 | Savarino |
| 2006/0269560 | A1 | 11/2006 | Savarino |
| 2007/0237791 | A1 | 10/2007 | Ranallo et al. |

FOREIGN PATENT DOCUMENTS

| EP | 368819 A1 * | 5/1990 |
| WO | WO 01/04148 | 1/2001 |
| WO | WO 02/059156 | 8/2002 |
| WO | WO 02/064162 | 8/2002 |
| WO | WO 2005/113827 | 12/2005 |

OTHER PUBLICATIONS

Lee et al. (Vaccine, 23:222-231, 2004).*
Peltola, H. et al., Prevention of traveller's diarrhoea by oral B-subunit/whole-cell cholera vaccine, Lancet, 1991, 338:1285-1289, Joseph Onwhyn, Britain.
Li X. et al., Use of translational fusion of the MrpH fimrial adhesin-binding domain with teh cholera toxin A2 domain, coexpressed with the colera toxin B Subunit, as an intranasal vaccine to prevent experiemental urinary tract infection by Protenus mirabilis, Infect. Immun., 2004, 72:7306-7310, the American Society for Microbiology, US.
Anantha, Ravi P. et al., Evolutionary and functional relationships of colonization factor antigen I and other class 5 adhesive fimbriae of ETEC *E.Coli*. Infect. and Immun. 2004. 72:7190-7201, the American Society for Microbiology, US.
Ahren and Svennerholm (1982), "Synergistic protective effect of antibodies against *Escherichia coli* enterotoxin and colonization factor antigens." Infect. Immun. 38:74-79.
Altboum et al. (2003), "Genetic characterization and immunogenicity of coli surface antigen 4 from enterotoxigenic *Escherichia coli* when it is expressed in a *Shigella* live-vector strain." Infect. Immun. 71:1352-1360.
Anderson et al. (2004), "An atomic resolution model for assembly architecture and function of the Dr adhesins." Mol. Cell 15: 647-57.
Barnhart et al. (2000), "PapD-like chaperones provide the missing information for folding of pilin proteins." Proc. Natl. Acad. Sci. USA 97(14): 7709-14.
Barry et al. (2003), "Immune responses elicited against multiple enterotoxigenic *Escherichia coli* fimbriae and mutant LT expressed in attenuated *Shigella* vaccine strains." Vaccine 17: 333-340.

(Continued)

*Primary Examiner* — Brian J Gangle
(74) *Attorney, Agent, or Firm* — McDonnell Boehnen Hulbert & Berghoff LLP

(57) ABSTRACT

The inventive subject matter relates to an immunogenic composition composed of a chimeric molecule including a conformationally stable adhesin from *Escherichia coli* fused to a bacterial toxin A subunit, such as cholera toxin A subunit or heat-labile *Escherichia coli* toxin A subunit. The invention also relates to the adhesin-toxin chimera noncovalently associated with a toxin B subunit of the same or different species as the A subunit. The invention also relates to a method of utilizing an adhesin/toxin fusion composition to elicit an immune response.

43 Claims, 8 Drawing Sheets

(56) References Cited

OTHER PUBLICATIONS

Figure 1:
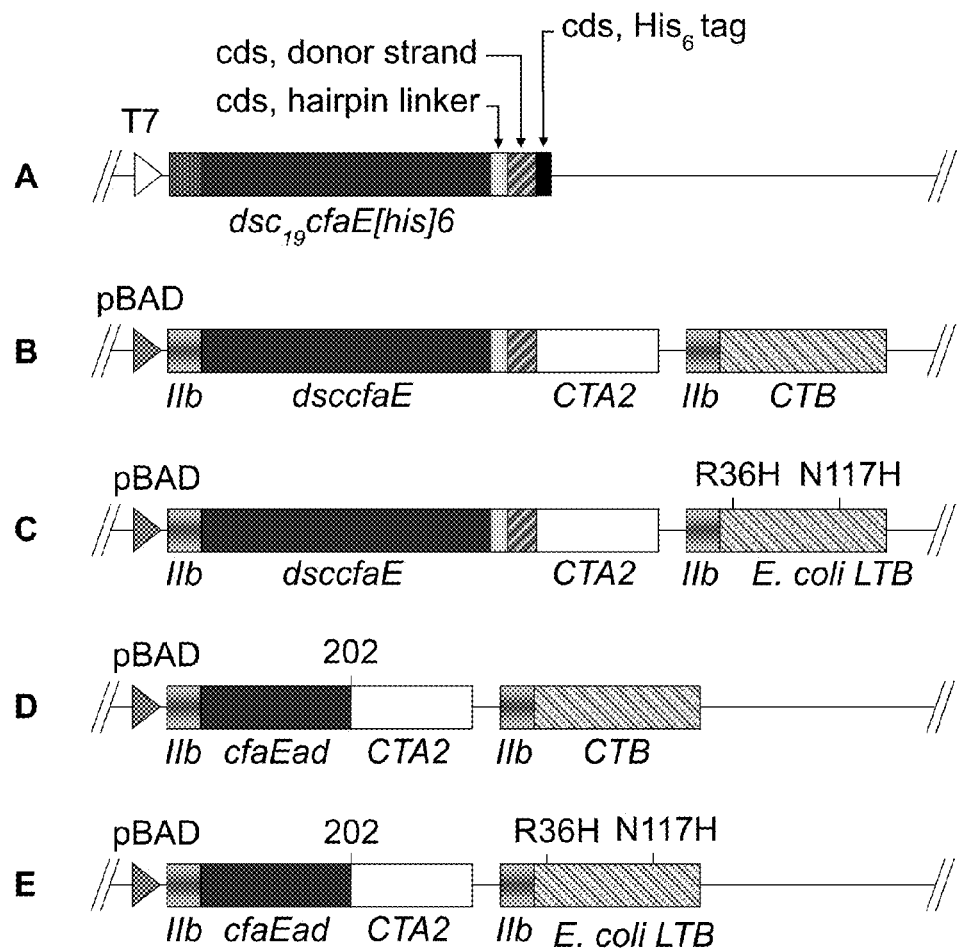

Bendtsen et al. (2004), "Improved prediction of signal peptides: SignalP 3.0." J Mol Biol 340:783-95.

Black (1990), "Epidemiology of travelers' diarrhea and relative importance of various pathogens." Rev Infect Dis 12 (Suppl 1):S73-S79.

Bowie et al. (1990), "Deciphering the message in protein sequences: tolerance to amino acid substitutions." Science 257: 1306-10.

Buhler et al. (1991), "Analysis of colonization factor antigen I, an adhesin of enterotoxigenic *Escherichia coli* 078: H11: fimbrial morphology and location of the receptor-binding site." Infect Immun 59:3876-3882.

Byrd et al. (2003), "Mucosal immunization of BALB/c mice using enterotoxigenic *Escherichia coli* colonization factors CFA/I and CS6 administered with and without a mutant heat-labile enterotoxin." Vaccine 21: 1884-93.

Choudhury et al. (1999), "X-ray structure of the FimC-FimH chaperone-adhesin complex from uropathogenic *Escherichia coli*." Science 285:1061-6.

Clemens et al. (1988), "Cross-protection by B subunit whole cell cholera vaccine against diarrhea associated with heat-labile toxin producing enterotoxigenic *Escherichia coli*: results of a large-scale field trial." J. Infect. Dis. 158: 372-377.

Cravioto et al. (1982), "Hemagglutination activity and colonization factor antigens I and II in enterotoxigenic and non enterotoxigenic *Escherichia coli* isolated from humans." Infect Immun 36:189-197.

Darfeuille-Michaud et al. (1990), "Adhesion of enterotoxigenic *Escherichia coli* to the human colon carcinoma cell line Caco-2 in culture." Infect Immun 58:893-902.

Dertzbaugh and Cox (1998), "The affinity of cholera toxin for Ni2+ ion." Protein Eng. 11: 577-581.

Domenighini et al. (1995), "Identification of errors among database sequence entries and comparison of correct amino acid sequences for the heat-labile enterotoxins of *Escherichia coli* and *Vibrio cholerae*." Mol. Microbiol 15: 1165-1167.

Evans et al. (1975), "Plasmid-controlled colonization factor associated with virulence in *Esherichia coli* enterotoxigenic for humans." Infect Immun 12:656-667.

Evans et al. (1978), "Detection and characterization of colonization factor of enterotoxigenic *Escherichia* coil isolated from adults with diarrhea." Infect Immun 19:727-736.

Froehlich et al. (1994), "CooC and CooD are required for assembly of CS1 pili." Mol Microbiol 12:387-401.

Froehlich et al. (1995), "Genes for CS2 pili of enterotoxigenic *Escherichia* coil and their interchangeability with those for CS1 pili." Infect Immun 63:4849-56.

Gaastra and Svennerholm (1996), "Colonization factors of human enterotoxigenic *Escherichia coli* (ETEC)." Trends Microbiol 4:444-452.

Gaastra et al. (2002), "Antigenic variation within the subunit protein of members of the colonization factor antigen I group of fimbrial proteins in human enterotoxigenic *Escherichia coli*." Int J Med Microbiol 292:43-50.

Grewal et al. (1997), "A new putative fimbrial colonization factor, CS 19, of human enterotoxigenic *Escherichia coli*." Infect Immun 65:507-513.

Hall et al. (1989), "Purification and analysis of colonization factor antigen I, *coli* surface antigen 1, and *coli* surface antigen 3 fimbriae from enterotoxigenic *Escherichia* coil." J Bacteriol 171:6372-6374.

Hess et al. (2002), "Identification and characterization of hydrophobic *Escherichia* coil virulence proteins by liquid chromatography-electrospray ionization mass spectrometry." Anal Biochem 302:123-130.

Hirst (1999), "Cholera toxin and *Escherichia coli* heat-labile enterotoxin," in E. Alouf and J. H. Freer (ed.), The Comprehensive Sourcebook of Bacterial Protein Toxins, 2 ed, vol. 6. Academic Press, San Diego, p. 104-129.

Holmes (1997), "Heat-labile enterotoxins (*Escherichia coli*)," In R. Rappuloi and C. Montecucco (ed.), Guidebook to Protein Toxins and Their use in Cell Biology. Oxford University Press, New York, p. 30-33.

Holmgren and Czerkinsky (2005), "Muscosal immunity and vaccines." Nat. Med. 11: S45-53.

Huilan et al. (1991), "Etiology of acute diarrhoea among children in developing countries: a multicentre study in five countries." Bull World Health Organ 69:549-55.

Hung et al. (1996), "Molecular basis of two subfamilies of immunoglobulin-like chaperones." EMBO J. 15:3792-3805.

International Search Report from International Application No. PCT/US2006/000660, International Publication No. WO 2006/076285, mailed on Jul. 25, 2008.

International Search Report from International Application No. PCT/US2007/000712, International Publication No. WO 2007/114878, mailed on Oct. 14, 2008.

Jalajalcumari et al. (1989), "Genes for biosysnthesis and assembly of CS3 pili of CFA/II enterotoigenic *Escherichia coli*: novel regulation of pilus production by bypassing an amber codon." Mol. Micro 3:1685-1695.

Jobling and Holmes (2005), "Activation of second messenger pathways by ADP-ribosylation of G-proteins," In T. Proft (ed.), Microbial Toxins: Molecular and Cellular Biology, Horizon Bioscience, Wymondharn, United Kingdom, p. 9-46.

Jordi et al. (1992), "The complete nucleotide sequence of region 1 of the CFA/I fimbrial operon of human enterotoxigenic *Escherichia coli*." DNA Seq 2:257-263.

Khalil et al. (1999), "Characterization of an enterotoxigenic *Escherichia coli* strain from Africa expressing a putative colonization factor." Infect Immun 67:4019-4026.

Khalil, Cassels, Shaheen, Pannell, Kamal, Pittner, Mansour, Frenck, Savarino, and Peruski (2000), Presented at the 100th General Meeting of the American Society for Microbiology, Los Angeles, CA, Abstract B-79.

Khandelwal et al. (2004), "Insecticidal pilin subunit from the insect pathogen Xenorhabdus nematophila." J. Bact. 186:6465-6476.

Krasan et al. (2000), "Evidence for donor strand complementation in the biogenesis of Haernophilus influenzae haemagglutinating pili." Mol. Micro. 35: 1335-47.

Kuehn et al. (1992), "P pili in uropathogenic *E. coli* are composite fibres with distinct fibrillar adhesive tips." Nature 356:252-5.

Levine et al. (1984), "Prevention of enterotoxigenic *Escherichia coli* diarrheal infection in man by vaccines that stimulate anti-adhesion (anti-pili) immunity," In E.C. Boedeker (ed.), Attachment of Microorganisms to the Gastrointestinal Mucosal Surface. CRC Press, Boca Raton, p. 223-244.

Low et al. (1996), "Fimbriae," In *Escherichia coli* and *Salmonella*: Cellular and Molecular Biology (Neidhardt et al. eds.), 2nd ed, vol. 1, ASM Press, Washington DC, pp. 146-157.

Nataro and Kaper (1998), "Diarrheagenic *Escherichia coli*." Clin Microbiol Rev 11:142-201.

[No Author Given], "International research sheds light on *Escherichia coli*." (Published Sep. 1, 2004) Medical Research News, http://www.news-medical.net.

Normark (2000), "Anfinsen comes out of the cage during assembly of the bacterial pilus." Proc. Natl. Acad. Sci. USA 97: 7670-7672.

Perez-Casal et al. (1990), "Gene encoding the major subunit of CS1 pili of human enterotoxigenic *Escherichia coli*." Infect Immun 58:3594-3600.

Perler (2002), "InBase, the Intein Database." Nuc. Acids. Res. 30:383-384.

Poole et al. (2007), "Donor strand complementation governs intersubunit interaction of fimbriae of the alternate chaperone pathway." Molecular Microbiology 63(5): 1372-84.

Qadri et al. (2005), "Enterotoxigenic *Escherichia coli* in developing countries: Epidemiology, microbiology, clinical features, treatment, and prevention." Clin. Microbiol. Rev 18: 465-483.

Ramer et al. (2002), "The Type IV pilus assembly complex: Biogenic interactions among the bundle forming pilus proteins of enteropathogenic *Escherichia coli*." J Bacteriol 184:3457-65.

Rao et al. (2003), "High disease burden due to enterotoxigenic *Escherichia coli* diarrhea in early life among rural Egyptian children." J Clin Microbiol 41:4862-4864.

Rao et al. (2005), "Serologic correlates of protection against enterotoxigenic *Escherichia coli* diarrhea." J. Infect. Dis. 1992: 562-570.

(56) References Cited

OTHER PUBLICATIONS

Sakellaris et al. (1996), "Assembly proteins of CS1 pili of enterotoxigenic *Escherichia coli*." Mol. Microbiol. 21:529-41.

Sakellaris and Scott (1998), "New tools in an old trade: CS1 pilus morphogenesis." Mol Microbiol 30:681-7.

Sakellaris et al. (1999), "A conserved residue in the tip proteins of CS1 and CFA/I pili of enterotoxigenic *Escherichia coli* that is essential for adherence." Proc Natl Acad Sci, USA 96:12828-12832.

Sakellaris et al. (1999), "The level of expression of the minor pilin subunit, CooD, determines the number of CS1 pili assembled on the cell surface of *Escherichia coli*." J Bacteriol 181:1694-7.

Sauer et al. (1999), Structural basis of chaperone function and pilus biogenesis. Science 285:1058-61.

Savarino et al. (1999), "Oral, inactivated, whole cell enterotoxigenic *Escherichia coli* plus cholera toxin B subunit vaccine: results of the initial evaluation in children. Pride Study Group." J. Infect. Dis. 179: 107-114.

Savarino, S.J., R. Abu-Elyazeed, M.R. Rao, R.W. Frenck, I. Abdel-Messih, H.E.R., S. Putnam, H. El-Mohamady, T. Wierzba, B. Pittner, K. Kamal, P. Moyer, M.B.Z., A.M. Svennerholm, Y.J. Lee, and J.D. Clemens (2003), Presented at the Sixth Annual Conference on Vaccine Research, Arlington, VA.

Schulz et al. (1997), "Disruption of the guanylyl cyclase-C gene leads to a paradoxical phenotype of viable but heat-stable enterotoxin-resistant mice." J. Clin. Invest. 100: 1590-1595.

Scott et al. (1992), "CooB is required for assembly but not transport of CS1 pilin." Mol Microbiol 6:293-300.

Smyth et al. (1996), "Fimbrial adhesins: similarities and variations in structure and biogenesis." FEMS Immunology and Medical Microbiology 16(2): 127-39.

Soto and Hultgren (1999), "Bacterial adhesins: common themes and variations in architecture and assembly." J Bacteriol 181:1059-1071.

Spangler (1992), "Structure and function of cholera toxin and the related *Escherichia coli* heat-labile enterotoxin." Microbiol. Rev. 56: 622-647.

Supplementary European Search Report from European Application No. EP 06717818, dated Jul. 31, 2009.

Supplementary European Search Report from European Application No. EP 07748881, dated Dec. 28, 2009.

Svennerholm et al. (1997), "Oral inactivated vaccines against enterotoxigenic *Escherichia coli*," In Levine et al. (ed.), New Generation Vaccines, II ed. Marcel Dekker, Inc., New York, p. 865-874.

Tinker et al. (2005), "Characterization of fluorescent chimeras of cholera toxin and *Escherichia coli* heat-labile enterotoxins produced by use of the twin arginine translocation system." Infect. Immun. 73: 3627-3635.

Turner et al. (2001), "Construction and characterization of genetically defined aro omp mutants of enterotoxigenic *Escherichia coli* and preliminary studies of safety and immunogencity in humans." Infect. Immun. 69: 4969-4979.

Verdonck et al. (2004), "Conserved regions in the sequence of the F4 (K88) fimbrial adhesion FaeG suggest a donor strand mechanism in F4 assembly." Vet. Micro 102: 215-225.

Viboud et al. (1996), "Binding of enterotoxigenic *Escherichia coli* expressing different colonization factors to tissue-cultured Caco-2 cells and to isolated human enterocytes." Microb Pathogen 21:139-147.

Yu et al. (2001), "Assembly of cholera toxin-antigen fusion proteins in transgenic potato." Transgenics 3: 153-62.

Zavialov et al. (2002), "Donor strand complementation mechanism in the biogenesis of non-pilus systems." Mol. Micro. 45: 983-95.

Zavialov et al. (2003), "Structure and biogenesis of the capsular FI antigen from *Yersinia pestis*: preserved folding energy drives fiber formation." Cell 113:587-596.

\* cited by examiner

ADHESIN-ENTEROTOXIN CHIMERA BASED IMMUNONGENIC COMPOSITION AGAINST ENTEROTOXIGENIC *ESCHERICHIA COLI*

CROSS-REFERENCE TO RELATED APPLICATIONS

This application is the national stage application of International Application No. PCT/US2007/000712, filed Jan. 11, 2007, and claims priority to U.S. Provisional Application No. 60/758,099 filed Jan. 11, 2006. The disclosures of these applications are incorporated by reference herein.

The disclosure of U.S. application Ser. No. 11/340,003, filed Jan. 10, 2006 is incorporated by reference herein.

PARTIES TO A JOINT RESEARCH AGREEMENT

The invention claimed herein was made by or on behalf of the United States of America as Represented by Secretary of the Navy and The Regents of The University of Colorado, a body corporate, who were parties to a joint research agreement.

SEQUENCE LISTING

I hereby state that the information recorded in computer readable form is identical to the written sequence listing.

FIELD OF INVENTION

The inventive subject matter relates to a method of inducing an immune response against enterotoxigenic *Escherichia coli* using a proteinaceous chimera molecule composed of bacterial fimbriae components and immunogenic bacterial toxins. The inventive composition contemplates *Escherichia coli* adhesin molecularly fused to diarrheagenic bacteria toxin yielding an adhesin-toxoid chimera.

BACKGROUND OF INVENTION

Enterotoxigenic *Escherichia coli* (ETEC), one of several pathotypes of diarrheagenic *E. coli*, causes a secretory-type diarrhea ranging from mild to cholera-like purging. ETEC poses an important medical concern to persons living in and travelers visiting many developing countries. ETEC is a principal cause of diarrhea in young children in resource-limited countries and also travelers to these areas (Black, 1990; Hui-lan, et al, 1991). Among infants and young children, the organism is estimated to cause 210 million cases of diarrhea and 380,000 deaths annually (Qadri, et al, 2005).

ETEC produce disease by adherence to small intestinal epithelial cells and expression of a heat-labile (LTI) and/or heat-stable (ST) enterotoxin (Nataro, et al, 1990). ETEC typically attach to host cells via filamentous bacterial surface structures known as colonization factors (CFs). More than 20 different CFs have been described, a minority of which have been unequivocally incriminated in pathogenesis (Gaastra and Svennerholm, 1996).

Firm evidence for a pathogenic role exists for colonization factor antigen I (CFA/I), the first human-specific ETEC CF to be described. CFA/I is the archetype of a family of eight ETEC fimbriae that share genetic and biochemical features (Evans, et al, 1975; Gaastra and Svennerholm, 1996; Grewal, et al, 1997; Khalil, et al, 2000). This family includes coli surface antigen 1 (CS1), CS2, CS4, CS14, CS17, CS19 and putative colonization factor O71 (PCFO71). The complete DNA sequences of the gene clusters encoding all eight members of this fimbrial family have been published (Froehlich, et al, 1994; Froehlich, 1995; Jordi, et al, 1992; Perez-Casal, et al, 1990; Scott, et al, 1992). The four-gene bioassembly operons of CFA/I and related fimbriae are similarly organized, encoding (in order) a periplasmic chaperone, major fimbrial subunit, outer membrane usher protein, and minor fimbrial subunit. CFA/I assembly takes place through the alternate chaperone pathway, distinct from the classic chaperone-usher pathway of type I fimbrial formation and that of other filamentous structures such as type IV pili (Ramer, et al, 2002; Soto and Hultgren, 1999). Based on the primary sequence of the major fimbrial subunit, CFA/I and related fimbriae have been grouped as Class 5 fimbriae (Low, et al, 1996).

Studies of CS1 have yielded details on the composition and functional features of Class 5 fimbriae (Sakellaris and Scott, 1998). The CS1 fimbrial stalk consists of repeating CooA major subunits. The CooD minor subunit is allegedly localized to the fimbrial-tip, comprising an extremely small proportion of the fimbrial mass, and is required for initiation of fimbrial formation (Sakellaris, et al, 1999). Contrary to earlier evidence suggesting that the major subunit mediates binding (Buhler, et al, 1991), recent findings, therefore, have implicated the minor subunit as responsible for fimbria-mediated adhesion and identified specific amino acid residues required for in vitro adhesion of CS1 and CFA/I fimbriae (Sakellaris, et al, 1999). The major subunits are responsible for serological distinctiveness of each fimbrae with the minor subunits (Gaastra, et al, 2002).

Comparative evolutionary analyses of Class 5 major and minor subunits demonstrate that greater structural conservation exists among the minor subunits as compared to the major subunits. This is consistent with ability of anti-minor subunit but not anti-major subunit or fimbrial antibodies to inhibit mannose-resistant hemagglutination (MRHA) of ETEC that express heterologous, subclass-related fimbriae (Anantha, et al, 2004).

Prior research efforts in uropathogenic *E. coli* strains, containing Type 1 and P fimbriae, have been used as models to elucidate the mechanisms of assembly of pili on these strains of bacteria. These studies showed that assembly in uropathogenic *E. coli* is effected via a chaperone-usher pathway (Kuehn, et al, 1992; Sauer, et al, 1999; Choudhury, et al, 1999). An outcome of this work has been development of the principle of donor strand complementation, a process in which fimbrial subunits non-covalently interlock with adjoining subunits by iterative inter-subunit sharing of a critical, missing β-strand (Sauer, et al 1999; Choudhury, et al 1999; Barnhart, et al, 2000). Evidence has implicated this same mechanism in the folding and quaternary conformational integrity of *Haemophilus influenzae* hemagglutinating pili (Krasan, et al, 2000), and *Yersinia pestis* capsular protein, a non-fimbrial protein polymer (Zavialov, et al, 2002). Both of these structures are distant Class I relatives of Type 1 and P fimbriae that are assembled by the classical chaperone-usher pathway.

Despite the efforts in uropathogenic *E. coli*, the identity of the adhesion moieties and the mechanism of fimbriae assembly in ETEC have been unclear. That the fimbrial assembly and structural components of these distinct pathways share no sequence similarity suggests that they have arisen through convergent evolutionary paths. Nevertheless, computational analyses of the CFA/I structural subunits suggest the possibility that donor strand complementation may also govern chaperone-subunit and subunit-subunit interaction.

The eight ETEC Class 5 fimbriae clustered into three subclasses of three (CFA/I, CS4, and CS14), four (CS1, PCFO71, CS17 and CS19), and one (CS2) member(s) (referred to as subclasses 5a, 5b, and 5c, respectively) (Anantha, et al, 2004). Previous reports demonstrated that ETEC bearing CFA/I, CS2, CS4, CS14 and CS19 manifest adherence to cultured Caco-2 cells (Grewal, et al, 1997; Viboud, et al, 1996). However, conflicting data have been published regarding which of the component subunits of CFA/I and CS1 mediate adherence (Buhler, et al, 1991; Sakellaris, et al, 1999).

This question of which fimbrial components is responsible for mediating adherence was approached by assessing the adherence-inhibition activity of antibodies to intact CFA/I fimbriae, CfaB (major subunit), and to non-overlapping amino-terminal (residues 23-211) and carboxy-terminal (residues 212-360) halves of CfaE (minor subunit) in two different in vitro adherence models (Anantha, et al, 2004). It was demonstrated that the most important domain for CFA/I adherence resides in the amino-terminal half of the adhesin CfaE.

The studies briefly described above provide evidence that the minor subunits of CFA/I, as well as the homologous subunits of other Class 5 fimbriae, are the receptor binding moiety (Sakellaris, et al, 1999; Anantha, et al, 2004). Consistent with these observations, because of the low levels of sequence divergence of the minor subunits observed within fimbrial subclasses 5a and 5b (Sakellaris, et al, 1999), the evolutionary relationships correlated with cross-reactivity of antibodies against the amino-terminal half of minor subunits representing each of these two subclasses (Anantha, et al, 2004).

Similar, but distinct from Class 5 fimbriae, coli surface antigen (CS3) represents the common adhesive fibrillae of the ETEC colonization factor antigen II (CFA/II) complex. ETEC expressing these antigens are prevalent in many parts of the world. CS3 is composed of two subunits, CstH and CstG. Furthermore, anti-sera against CstH, but not CstG, exhibited hemagglutination inhibition, suggesting that the CstH was the CS3 adhesin.

The CS3 fibrillar assembly has been classified as a member of the classical chaperone-usher (CU) pathway based on the genetic relatedness of the CS3 periplasmic chaperone to the PapD superfamily (Hung, et al, 1999). Interestingly, it falls into the FGL (F1-G1 long) subfamily, referring to a characteristic structural feature of the chaperone, which mediates assembly of thin fibrillar or afimbrial adhesive organelles (Soto and Hultgren, 1996). Alignment of the N-terminal amino acid span of CstH with *Yersinia pestis* F1 capsule subunit reveals a common motif of alternating hydrophobic residues through amino acid 16 (with reference to the mature CstH polypeptide). This span of the F1 capsular subunit (Caf1) functions as the donor strand, interacting with the Caf1M chaperone and neighboring F1 protein subunits during capsular assembly and subunit articulation (Zavialov, et al, 2003). Therefore, it is logically reasoned that CstH may function in a similar manner.

Cholera toxin (CT) and *E. coli* enterotoxins (LTI and LTII) are members of the heat-labile enterotoxin family (Hirst, 1999; Holmes, 1997; Jobling and Holmes, 2005). They act on enterocytes of the small intestine and cause secretory diarrhea. Each toxin consists of a single A polypeptide and five identical B polypeptides all attached by noncovalent interactions. The known variants of CT and LTI belong to serogroup I and variants of LTII to serogroup II.

Structures of CT, LTI and LTIIb show that all have closely related folding patterns, despite differences in amino acid sequences between the B polypeptides of toxins in serogroups I and II (Domenighini, et al, 1995). The five identical B polypeptides form a doughnut-shaped module. The A polypeptide has an A1 domain located next to the upper face of the B subunit and an A2 domain that penetrates the central pore of the B pentamer. A1 and A2 are joined by a short surface-exposed loop. Proteolytic cleavage within that loop generates nicked holotoxin, with fragments A1 and A2 remaining linked by a disulfide bond. Five identical binding sites on the lower face of the B pentamer interact with specific receptors on target cells. The receptor-binding specificities among the enterotoxins differ greatly. CT and LTI bind tightly to ganglioside GM1. LTI, but not CT, binds to asialoganglioside GM1 and certain glycoproteins, and LTIIa and LTIIb bind best to gangliosides GD1b and GD1a, respectively.

The activity of enterotoxins on cells, such as epithelial cells upon colonization by ETEC, is mediated by an intricate sequence of events (Hirst, 1999; Holmes, 1997; Jobling and Holmes, 2005; Spangler, 1992). Upon colonization, ETEC heat-stable (ST) and/or heat-labile (LTI) enterotoxin act upon epithelial cells. In addition to LTI, ETEC heat-stable enterotoxin (ST) is a nonimmunogenic peptide analog of the intestinal peptide guanylin that activates intestinal membrane-bound guanylate cyclase (Schulz, et al, 1997).

Seroepidemiologic studies of young children has shown an inverse correlation between serum anti-CFA/I IgG antibody levels and a risk of disease with CFA/1-ETEC (Rao, et al, 2005). However, studies have failed to demonstrate that anti-LTI antibodies are protective. Evidence exists that administration of the B subunit of CT (CT-B) confers significant protection against ETEC caused diarrhea, which express the antigenically similar LTI enterotoxin (Clemens, et al, 1988; Peltola, et al, 1991). Furthermore, animal challenge studies have suggested that anti-fimbrial and anti-LTI antibodies act synergistically to protect against ETEC challenge (Ahren and Svennerholm, 1982).

Because of the promising immune responses to CFA/I and other coli surface antigens with nontoxic forms of LTI or CT, these antigens have been the focus of mucosal vaccine formulations against ETEC (Holmgren and Czerkinsky, 2005). An oral, killed whole-cell ETEC vaccine co-administered with CT-B has been extensively tested (Savarino, et al, 1999; Svennerholm, et al, 1997). Although the vaccine was found to be safe, it was not efficacious in infants (Savarino, et al, 2003). Furthermore, live attenuated ETEC vaccines have not proven effective partly due to the lack of achieving a proper balance between attenuation and immunogenicity (Altboum, et al, 2003; Barry, et al, 2003; Levine, et al, 1984; Turner, et al, 2001). Therefore, the importance of identification of the fimbrial component that might more effectively induce anti-adhesive immunity has become ever more acute. In ETEC, this moiety has been shown to be the minor fimbrial subunits, such as CfaE. Therefore, an aspect of this invention is the construction and use of conformationally stable ETEC fimbrial adhesins or adhesin domains in conjunction with components of bacterial toxins, such as CT or LT, to induce immunity against diarreheagenic ETEC.

SUMMARY OF THE INVENTION

Enterotoxigenic *Escherichia coli* (ETEC) are one of several important pathotypes of *E. coli* and one of the most important of the diarrheagenic *E. coli* strains. The organisms cause a secretory-type diarrhea ranging from mild to cholera-like purging. Currently, no efficacious vaccine exists against ETEC. Therefore, new vaccine formulations against these organisms are critical, especially for developing countries where diarrheal diseases are most prevalent and medical infrastructure is limited.

An object of the invention is a composition comprising a conformationally-stable and protease resistant adhesin polypeptide-toxin fusion constructs for use in vaccine formulations. The contemplated fusion construct contains any bacterial toxin A subunit. Additionally, a contemplated version contains the A subunit, contained in the fusion product, in noncovalent association with a toxin B subunit of the same or different toxin. The composition is useful for the induction of an immune response against *Escherichia coli*. Examples of toxins include cholera toxin and enterotoxigenic *Escherichia coli* heat-labile enterotoxin.

A further object of the invention is a conformationally-stable and protease resistant adhesin polypeptide-bacterial toxin A subunit fusion construct, with or without noncovalent association with a toxin B subunit, wherein the toxin A an B subunits are derived from cholera toxin or *E. coli* heat-labile toxin.

A still further object of the invention is a method of inducing an immune response against *Escherichia coli* fimbriae or *Escherichia coli*, including Class 5 *E. coli* and *E. coli* CS3 fibrillae, by administration of a chimeric molecule or mixture of chimeric molecules, each composed of a stabilized ETEC adhesin polypeptide genetically fused to component of a bacterial toxoid, such as from cholera or ETEC heat-labile toxin, that exhibits immunomodulatory and adjuvant effects.

An additional object is the prevention of colonization of Escherichia coli by inhibiting adherence of ETEC fimbriae or fibrillae to host cells.

A further, additional object is the induction of an antibody immune response against enterotoxin by the by administration of a chimeric molecule or mixture of chimeric molecules, each composed of a stabilized ETEC adhesin polypeptide genetically fused to component of a bacterial toxoid, such as from cholera or ETEC heat-labile toxin.

These and other objects of the invention are accomplished by employing *Escherichia coli* adhesin polypeptides as a vaccine component to induce immunity.

BRIEF DESCRIPTION OF THE DRAWINGS

FIG. 1. Maps of plasmid inserts that encode the adhesin-entertoxoid chimeras. From top to bottom of the figure: T7-based clone from which the dscCfaE gene was amplified in the construction of the two following plasmid inserts; pBAD-based clone for dscCfaE-CTA2/CTB5 chimera expression; pBAD-based done for dscCfaE-CTA2/LTB5 chimera expression; and the planned inserts for expression of chimera proteins in which the CfaE adhesin domain (CfaEad) constitutes the adhesin component.

FIG. 2. Maps of two chimera expression plasmids. (A) Plasmid p0809C3 was constructed and used for production of the dscCfaE-CTA2/CTB5 chimera, and (B) p1121C1 was constructed and used for production of the dscCfaE-CTA2/LTB5 chimera. Each features a p15A origin of replication, chloramphenicol resistance marker (cat), and an arabinose-inducible promoter (pBAD) upstream of the tandem genes encoding eh adhesin-CTA2 fusion and B-enterotoxoid.

FIG. 3. Inhibition of CFA/I ETEC-induced MRHA.

FIG. 4. Murine serum IgG responses to CfaE after immunization with CfaE-CTA2/CTB chimera.

FIG. 5. Mouse serum IgG response to CfaE after intranasal immunization with CfaE-CTA2/CTB chimera.

FIG. 6. Mouse serum IgA responses to CfaE after intranasal immunization with CfaE, an admixture of CfaE plus CTB or CfaE-CTA2/CTB.

FIG. 7. Two-step purification of CfaE-CTA/CTB chimera by (A) Talon chromatography followed by (B) gel filtration.

FIG. 8. Binding of chimera to immobilized GM1.

DETAILED DESCRIPTION OF PREFERRED EMBODIMENTS

Design and Construction of Adhesin-Toxin Chimeras

The present invention relates to methods and a biological composition for the induction of anti-adhesive immune responses by the administration of conformationally stable, and thus immunologically active, adhesin polypeptide. Adhesins contemplated in the inventive composition include, but are not limited to, those from Class 5 fimbriae and from CS 3 (i.e., CstH). Adhesin, the distal molecular component of enterotoxigenic *Escherichia coli* fimbriae and fibrillae, are the likely effectors for bacterial attachment to host cells (Anantha, et al, 2004). Therefore, adhesins are critical for bacterial colonization and pathogenicity.

Polypeptide sequences from a number of pathogenic bacterial species, such as LT or CT, have been shown to be potent immunomodulators. Furthermore, CT B-subunit (CTB) confers significant protection against ETEC caused diarrhea (Clemens, et al, 1988; Peltola, et al, 1991). Consequently, concomitant administration of adhesin with bacterial toxin may provide greater protective immunity against diarrheagenic bacteria than formulations containing other ETEC moieties. The current invention provides a composition and method of using said composition for the induction of immunity, principally immunoglobulin-mediated, that specifically binds to bacterial adhesin to disrupt colonization of diarrheagenic bacteria by inhibiting activity of the bacterial adhesin and decreases the contribution of heat-labile entertoxins to diarrhea both by inhibiting activity of heat-labile enterotoxin and as a secondary effect of preventing bacterial colonization and thereby decreasing production of both heat-labile and heat-stable enterotoxins, in vivo.

Conformational stability, and potentially protease resistance of adhesin polypeptides is important to ensure maximum immunogenicity. Conformational integrity of adhesin monomers is conferred by a donated β-strand provided by an adjacent subunit. In Class 5 fimbriae, for example, conformational stability of the CFA/I adhesin, CfaE, is provided by the donor β-strand from CfaB. In CS3, stability can also be provided by peptide donor strands from adjacent monomers. In this regard, CstH donor strand provides stability to adjacent CstH adhesin monomers.

An aspect of the invention is a chimeric molecule with conferred conformational stability of an adhesin polypeptide in juxtaposition with bacterial toxins subunits, such as from LT or CT. In order to ensure conformational stability of adhesin polypeptide immunogens, with concomitant improved efficacy of vaccines, an aspect of this invention is polypeptide constructs designed to operatively provide a donor β-strand to adjacent adhesin polypeptide sequences that are operatively fused to toxin protein or polypeptide. The adhesin component of the constructs are composed of adhesin polypeptides linked at the C-terminal end to a linker polypeptide, which is in turn linked, at the C-terminal end, to a donor strand polypeptide. Donor strand can be provided by a number of sources including all or a portion of a major fimbrial structural subunit, such as CfaB. The adhesin component is then genetically fused to a polypeptide derived from a bacterial toxin A subunit. The inventive chimera can also be expressed in conjunction with the toxin B subunit, such that the expressed chimera containing the toxin A subunit component then assemble with the toxin B subunits to form a chimeric enterotoxin-like molecule.

The inventive composition contemplates a composition that is composed of any adhesin polypeptide, such as CfaE, CsfD, CsuD, CooD, CosD, CsdD, CsbD, CotD and CstH. The adhesin is then fused at the C-terminal end of adhesin to a donor strand via a linker polypeptide. The donor strand can come from any number of sources including major fimbrial subunits such as CfaB, CsfA, CsuA1, CsuA2, CooA, CosA, CsbA, CsdA, CotA and CstH. Such conformationally stabilized adhesin are herein described with the prefix "dsc." The inventive composition further contemplates that the conformationally stabilized adhesin is in-turn fused with a bacterial toxin A subunit, as illustrated in FIG. 1. An additional extension of the inventive composition contemplates the use of only the N-terminal domain of the native adhesin structure as the stable adhesin component of the inventive composition. Such conformationally stable adhesin domains are herein described with the suffix "ad", and without the prefix "dsc."

Examples of conformationally stabilized adhesin include, but are not limited to, dscCfaE (SEQ ID No. 6); dscCsbD (SEQ ID No. 12); dscCotD (SEQ ID No. 15), which contain a donor strand from CfaB, CotA and CotD, respectively. Additionally, non-Class 5 fimbrae adhesins can be used, such as CstH by fusing the leader sequence (SEQ ID No. 27) to the N-terminal region of CstH (SEQ ID No. 28) and fusing this, via a linker (SEQ ID No. 1), to a donor strand from CstH (SEQ ID No. 29). The stable, dscCstH, sequence is illustrated in SEQ ID No. 30.

Figure 2:
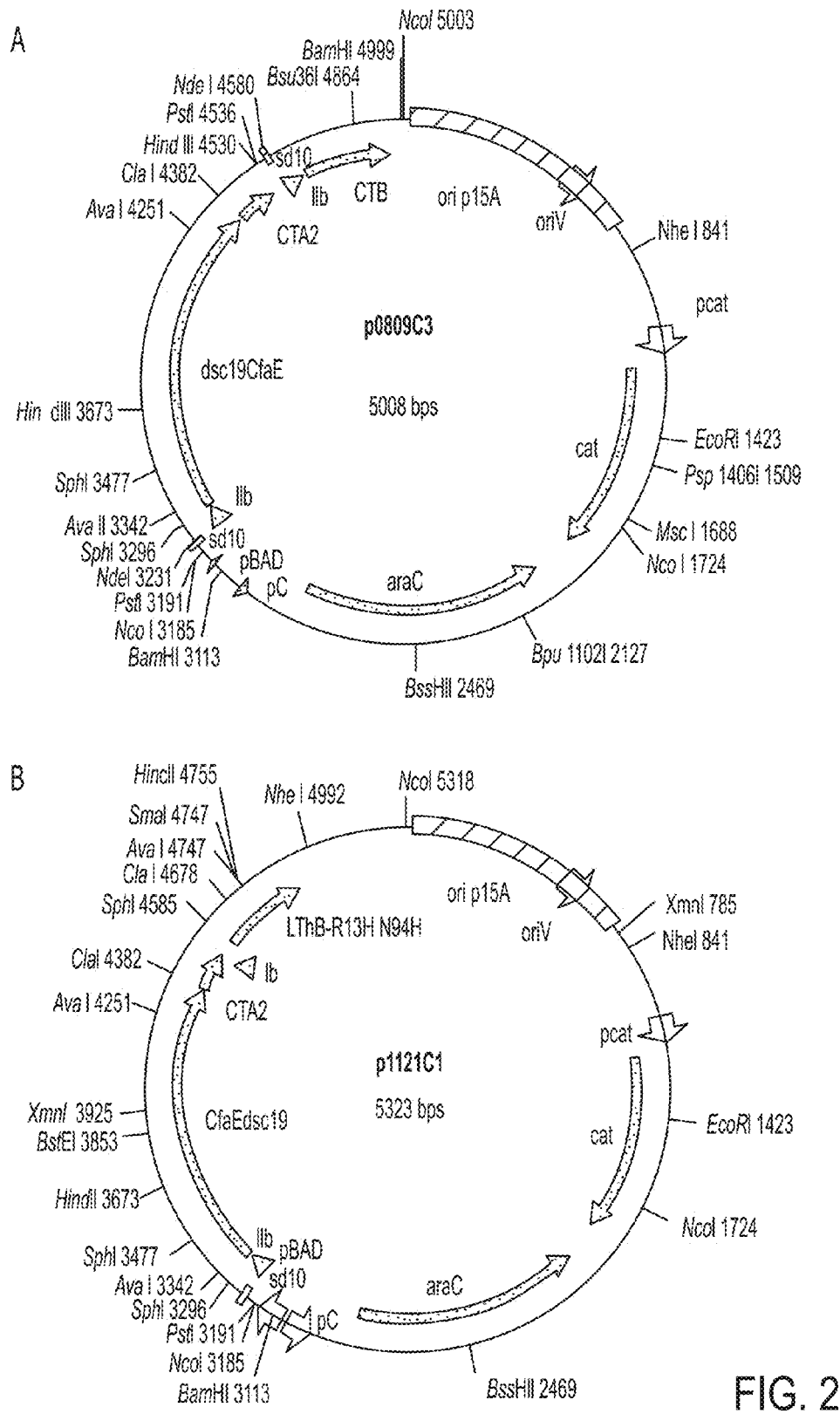

The conformationally stable adhesin is then fused to a full-length or truncated A2 bacterial toxin A subunit. The inventive composition contemplates that any of a number of bacterial toxin A subunits can be used. Examples of A subunits include, but are not limited to LTA2 (SEQ ID No. 18) and CTA2 (SEQ ID No. 19). Additionally, the inventive composition contemplates the ability to coordinately and concomitantly express the stabilized adhesin-toxin A subunit chimera with a toxin B subunit, either under a single operon, as illustrated in FIG. 2 or as gene products expressed from separate promoters either on a single plasmid or on separate but compatible plasmids, such that the adhesin-toxin A subunit and B subunits can spontaneously molecularly interact and assemble into an toxin-like molecule. The A and B subunits can be from the same or different bacterial species. Examples of toxin B subunits include, but are not limited to CTB (SEQ ID No. 21) and LTB (SEQ ID No. 23). The B subunit can contain an LTIIb leader sequence (SEQ ID No. 24) for improved expression as in SEQ ID No. 20 and SEQ ID No. 22, for CTB and LTB, respectively. Furthermore, the N-terminal five (5) amino acids of either CTA2 or LTA2 can be substituted for the amino acid sequences of SEQ ID Nos. 25 and 26. Table 1 summarizes the sequences.

TABLE 1

| SEQ ID number | Description |
|---|---|
| 1-3 | Linkers |
| 4 | CfaE |
| 5 | CfaB donor strand |
| 6 | dscCfaE |
| 7 | CfaEad |
| 8 | Signal sequence of dscCfaE (LTIIb) |
| 9 | dscCfaE (with aa subst from K to N) |
| 10 | dscCfaE (with aa subst from K to S) |
| 11 | dscCfaE (with aa subst from K to T) |
| 12 | dscCsbD |
| 13 | CsbDad |
| 14 | Signal sequence for CsbD (LTIIb) |
| 15 | dscCotD |
| 16 | CotDad |

TABLE 1-continued

| SEQ ID number | Description |
|---|---|
| 17 | Signal sequence for CotD (LTIIb) |
| 18 | LTIA2 polypeptide |
| 19 | CTA2 polypeptide |
| 20 | CTB polypeptide with leader |
| 21 | CTB polypeptide with no leader |
| 22 | LTIB polypeptide with leader |
| 23 | LTIB polypeptide with no leader |
| 24 | LTIIb signal sequence |
| 25 | Variant 1 of N-terminal region of LTIA2 or CTA2 |
| 26 | Variant 2 of N-terminal region of LTIA2 or CTA2 |
| 27 | CstH signal peptide |
| 28 | CstH |
| 29 | CstH donor strand |
| 30 | dscCstH |
| 31 | LTIA2-variant |
| 32 | LTIA2-C199S |
| 33 | CTB El tor |
| 34 | CTA2 trucated |
| 35 | LTIA2 Truncated |

EXAMPLE 1

Construction of dscCfaE-CT and LT Chimeras

In order to more fully illustrate the invention, an example of an anti-ETEC composition containing CfaE, the minor subunit of CFA/I, is described. Referring to FIG. 1 (A), a conformationally stable CfaE was constructed by genetically joining a hairpin linker to the 3' end of the coding sequence of CfaE. The amino acid sequence of the linkers is described by SEQ ID No. 1, 2 and 3. An amino acid donor strand from CfaB, described in SEQ ID No. 5, was then joined at the 3' end of the linker and finally a hexahistidine tag was joined at the 3' end of the CfaB donor strand. The construct was then inserted in pET24 plasmids and expressed in E. coli bacteria. The resultant polypeptide, referred to as dscCfaE, was purified by nickel or cobalt affinity and cation-exchange chromatography. The recombinant polypeptide was soluble and stable. Based on gel filtration, the dscCfaE polypeptide existed as a monomer and CD spectroscopic analysis yielded results consistent with the existence of a predominantly β-stranded molecule.

Referring to FIG. 1, the A2 fragment of the cholera toxin A subunit was genetically fused to the carboxyl-terminus (C-terminus) dscCfaE. It should be noted, however, that instead of the A2 fragment of CTA, the A2 fragment, from the A subunit of other toxins can be used, such as LT-I. In order to facilitate purification of the monomeric dscCfaE, a Histidine (His-6) tail was added to the C-terminus of dscCfaE. See FIG. 1A). However, in order to facilitate purification of chimera with minimal modification of native sequence, in other constructs, His was substituted at selected sites within the toxin sequences of LT. However, because the pentameric B subunit of CT binds spontaneously to nickel or cobalt, either the CTB pentamer alone or an antigen construct that contains both a chimeric adhesin-CTA2 fusion polypeptide and the CTB pentamer can be purified directly by nickel or cobalt affinity chromatography without the need to add His-6 tag either to the adhesin-CTA2 fusion polypeptide or to the CTB polypeptide. Therefore, the coding region for the His-6 tag in dscCfaE was not included in the construct shown in FIG. 1B. Unlike pentameric CTB, the pentameric B subunit of LT-I does not bind spontaneously either to nickel or cobalt containing resins. However, introducing R13H and N94H substitutions into the sequence of the mature LT-1B polypeptide enables pentameric LT-1 B (or a corresponding antigen construct containing both a chimeric adhesin-CTA2 fusion polypeptide and the LT-IB pentamer) (the reader is referred to FIG. 1C) to bind to nickel or cobalt-containing resins and to be purified by nickel or cobalt affinity chromatography.

Furthermore, since the adhesin domain is stabilized by two intradomain disulfide bridges, placement of a stop codon after CfaE residue 199 to 204 results in production of a stable one-domain adhesin that lacks the pilus-forming domain of the original two-domain two-domain adhesin. Adhesin monomer with a stop codon introduced at this point contains the suffix "ad", for example CfaEad (SEQ ID. No. 7); CsbDad (SEQ ID. No. 13) and CotDad (SEQ ID No. 16). The coding sequence for the corresponding stable one-domain adhesin can therefore be used in place of the coding sequence for the stable two-domain dsc-adhesin variant to produce antigen constructs in which the adhesin-ad-CTA2 fusion polypeptide replaces the dsc-adhesin-CTA2 fusion polypeptide described above (see FIGS. 1D and 1E).

Referring to FIG. 1, when the coding regions for an adhesin-CTA2 fusion protein and a bacterial toxin B subunit are both present within an operon in the expression plasmid the adhesin-toxin A subunit chimera as well as a toxin B subunit are produced concomitantly. This permits both the expressed A and B toxin subunit polypeptides to be secreted into the periplasm of the *E. coli* host cell and to assemble spontaneously in the periplasm to form the desired chimeric enterotoxin-like antigen. The A and B subunits can be from the same or different bacterial species. As a further illustration, FIGS. 2A and 2B show a maps of a plasmids encoding a chimera constructs that contain the pentameric B subunits from CT and from LT-1, respectively.

FIG. 1 shows a dscCfaE-CTA2 fusion that is coordinately expressed with either the B subunit of cholera toxin or *E. coli* LT. The addition of LTIIB signal sequence enhances the likely expression of recombinant products since recombinant LTIIb is produced at a level of almost 100-fold over recombinant CT or CTB. In order to facilitate construction of CT-like chimeras, the expression vectors were modified by adding the coding region for CTA2 immediately downstream and in frame with the adhesin gene sequence so that the protein of interest is not only secreted into the periplasm but also contains the A2 polypeptide of CT at its C-terminus.

The coding sequence for dscCfaE was cloned in-frame into two vectors for expression of an A1 replacement antigen with an N-terminal LTIIb-B signal sequence and a C-terminal A2 fusion, upstream from the cholera toxin B subunit gene. The pLDR5 and pARLDR19 vectors place the modified cholera toxin operon under the control of a lac promoter or an arabinose-inducible pBAD promoter. (p0809C3), respectively. These clones were transformed into appropriate *E. coli* strains for expression. Both constructs produced chimera in the periplasm when grown in rich medium under inducing conditions.

Figure 8:
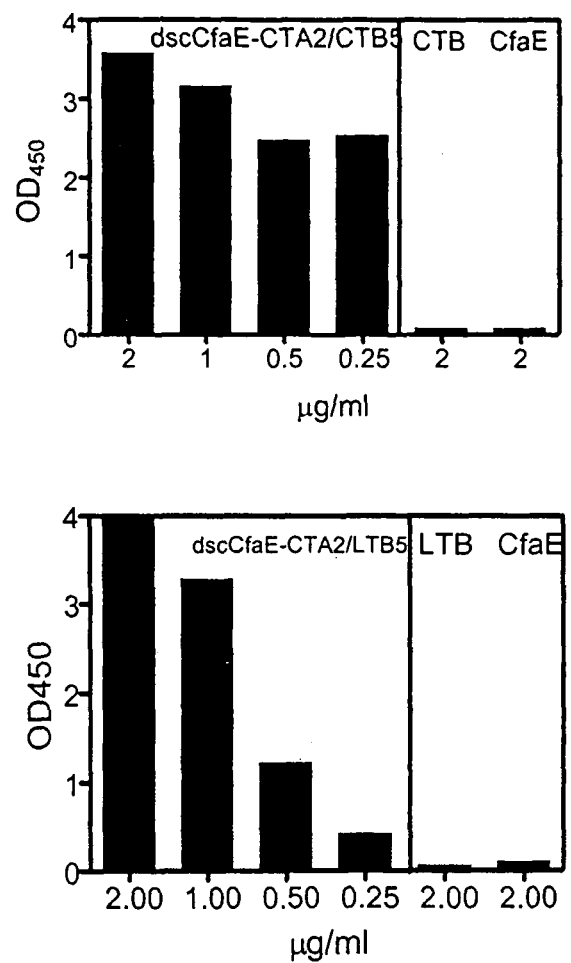

After induction, cells were treated with polymyxin B to release periplasmic contents and the soluble fraction was purified by metal affinity chromatography (Dertzbaugh and Cox, 1998). Free CTB pentamer were separated from dscCfaE-CTA2/CTB chimera by gel filtration. Analysis of the chimera by SDS-PAGE and Western blot using antibodies specific for CTA, CTB and CfaE showed an anti-CTB-reactive band and a dscCfaE-CTA2 fusion protein band that reacted with both anti-CTA and anti-CfaE antisera. Referring to FIG. 8, using a 96-well ELISA format with GM1 coated plates and detection with a primary anti-CfaE antibody, we demonstrated that dscCfaE-CTA2/CTB chimeras indeed bound to GM 1.

As a further functional enhancement of expressed product, since the N-terminus of CTA2 occurs at residue 194, the sole cysteine-199 residue was changed in CTA2 to serine in order to prevent any aberrant disulfide bond formation between cysteine-199 and other cysteines in the antigen domain of the antigen-CTA2 fusion protein. Additionally, other vectors can be made, such as pARLDR19, for enhanced production of chimeras under the control of the arabinose-inducible pBAD promoter instead of the lac promoter (Tinker, et al, 2005; Li, et al, 2004).

EXAMPLE 2

Functional Analysis of Chimera Constructs

The constructs were functionally examined. The construct in FIG. 1A or FIG. 1B was adsorbed onto 3 μm latex beads and added to human or bovine red cells with the resultant induction of MRHA. This observation provides clear evidence that CfaE is the adhesin in ETEC.

Crystallographic analysis of dscCfaE at 2.3 Å resolution revealed two elongate domains joined by a loop near its midpoint. Both the N-terminal and C-terminal domains form a β-sheet structure and the donor β-strand from CfaB fills a hydrophobic groove of the C-terminal domain stabilizing the molecule. The adhesin domain is stabilized by two intradomain disulfide bridges. Placement of a stop codon after CfaE residue 199 (refer to FIG. 1C) will yield a stable CfaE adhesion domain (designated CfaE-ad).

The antigenicity and immunogencity of dscCfaE were tested in animal models. Initially two rabbits were immunized parenterally with a four-dose (0, 28, 56 and 84 days) regimen of 250 μg per dose with Freund's adjuvant. Serum drawn 28 days after the last boost exhibited high anti-CfaE titers in each rabbit as measured by CfaE enzyme-linked immunosorbent assay (ELISA). Moreover, in a hemagglutination inhibition (HAI) assay, these antisera inhibited MRHA of ETEC that express CFA/I as well as CS4 and CS14 fimbriae.

A mouse experiment was conducted to determine the relative mucosal immunogenicity of dscCfaE in comparison to CFA/I fimbriae. Groups of 6 mice were given 25 μg of the test antigen either alone or co-administered with 1.5 μg of genetically detoxified LTR192 mucosal adjuvant, intranasally (IN). Another cohort of mice were immunized orogastrically at a dose of 250 μg with or without 10 μg of LTIR 192G. All animals received a 3-dose schedule at 2 week intervals. Robust titers were observed by ELISA when the immobilized antigen was homologous with the antigen used for immunization. In a head-to-head comparison of anti-adhesive antibody levels by the HAI assay, the dscCfaE immunized groups exhibited significantly higher titers of HAI antibody than the corresponding CFA/I immunized groups. Taken together, these animal studies suggest that CfaE is capable of inducing serum antibody responses upon parenteral or mucosal (IN) immunization. Furthermore, the antigen is superior to CFA/I in eliciting functional anti-adhesive antibodies.

Figure 3:
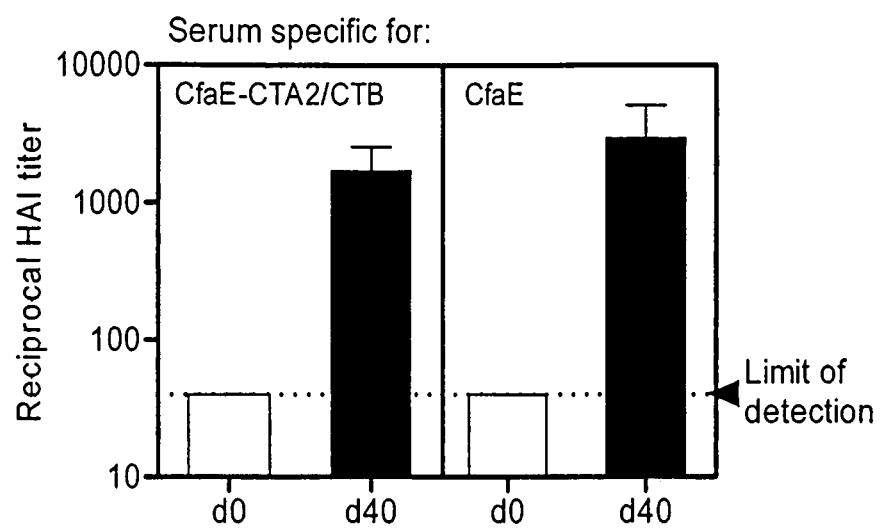

Other murine immunization studies were conducted to evaluate the chimera's anitgenicity, specifically its capacity to induce an anti-adhesive antibody response and to evaluate the immunomodulatory properties of the dscCfaE-CTA2/CTB chimera upon IN immunization. In the antigenicity study, three groups of mice (n=3 per group) were immunized intraperitoneally (IP) with a two-dose regimen of dscCfaE-CTA2/CTB chimera, or dscCfaE alone or CTB alone at 0 and 28 days, with approximately 50 μg primary and 25 μg booster dose of the relevant antigen. Serum was collected pre-immunization and 12 days after the booster dose (day 40) and tested for in vitro inhibition of MRHA by incubation of a standard concentration of CFA/I-ETEC (strain H10407) with serial dilutions of antiserum before addition to human red cells and a determination of HAI activity. None of the preimmunization sera showed HAI activity at the minimum dilution tested (1:20) nor did post-immunization sera from CTB immunized mice. In contrast, serum from both the dscCfaE and dscCfaE-CTA2/CTB immunized groups inhibited MRHA at similar dilutions, as illustrated in FIG. 3. These corresponded to high serum anti-CfaE IgG titers as measured by ELISA at day 40 in both groups. The CfaE group geometric mean titer was 423,000 and the dscCfaE-CTA2/CTB group geometric mean titer was 233,000. Therefore, dscCfa-CTA2/CTB chimera effectively presents the adhesin for induction of functional antibody responses.

Figure 4:
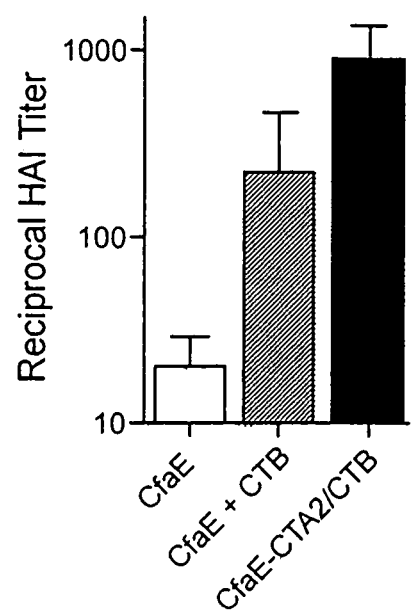
Figure 5:
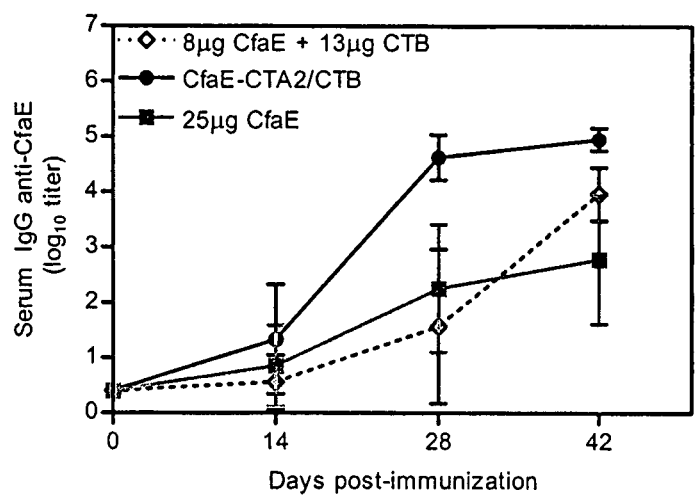

Referring to FIG. 4, five groups of mice (n=10 per group) were immunized IN at 0, 14, and 28 days with the following antigens: (1) dscCfaE-CTA2B (20 μg total weight calculated to give 8 μg CfaE and 11 μg CTB); (2) dscCfaE (8 μg)+CTB (13 μg) admixed; (3) dscCfaE alone (25 μg); (4) CTB alone (13 μg); and (5) PBS negative control. Serum IgG antibody titers to CfaE and CTB were determined by ELISA at 0, 14, 28 and 42 days. Mouse serum hemagglutination inhibition was examined subsequent to IN administration of CfaE chimeras. As illustrated in FIG. 4, like in FIG. 3, HAI titers were significantly higher than each of the other groups at day 42. Additionally, referring to FIG. 5, all groups receiving CTB in any form exhibited high serum anti-CTB titers by day 42, as expected. The dscCfaE-CTA2/CTB chimera group showed a significantly higher serum IgG anti-CfaE response than either the CfaE+CTB admixture or the dscCfaE groups measured at days 14, 28 and 42.

Figure 6:
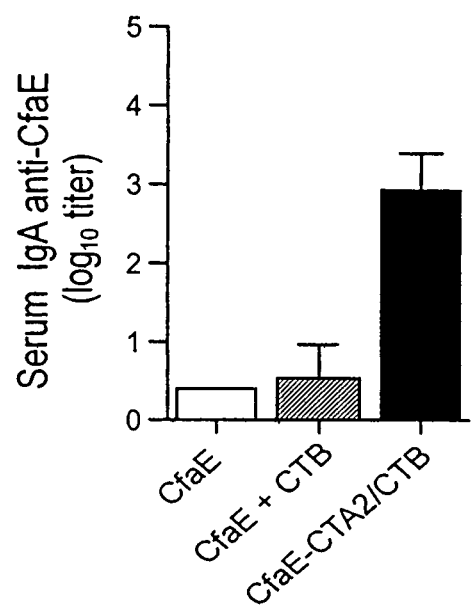

In addition to IgG, IgA titers were also examined following administration of dscCfaE-CTA2/CTB5. Anti-CfaE titers were measured by ELISA on day 0 and day 42 and are illustrated in FIG. 6. IgA titers at baseline (day 0) were below the limit of detection for all groups in FIG. 5. The result, as illustrated in FIG. 6, shows that the chimera group yielded a significantly higher titer of IgA than the other groups.

EXAMPLE 3

Potential Use of Inventive Chimera in Vaccine Formulations

The adhesins are likely the most important component for the induction of immunity against diarrheagenic *E. coli*, although preventing the activity of the heat-labile enterotoxin may also contribute to protection. Because the fimbrial adhesins are inherently unstable and subject to degradation when devoid of their non-covalent linkage to adjacent subunits, the current invention significantly improves the immunogenic potential of adhesin by conferring conformational stability. Additionally, the immunogenic efficacy of conformationally stable adhesin is likely improved significantly by providing the adhesin construct as a chimera with enterotoxin components that have both potent immunogenicity and adjuvant activity.

The inventive construct is anticipated to be useful as a vaccine component for the induction of an immune response and/or anti-toxic immunity against diarrheagenic *E. coli*. The method for induction of immunity contains the following steps:
 a. priming by administration of immunogen comprising a chimeric polypeptide containing a conformationally stable two-domain or one-domain adhesin fused component fused to an intact or truncated A2 polypeptide derived from a toxin A subunit. The immunogen can also comprise the chimeric polypeptide, assembled into an enterotoxin-like chimera by noncovalent interactions between its intact or truncated A2 polypeptide with the toxin B subunit polypeptides. The toxin A and B subunits can be derived from any bacterial toxins, for example *Vibrio cholerae* or *E. coli* heat-labile enterotoxin. The range of a unit dose of immunogen is 50 μg to 1 mg, and can be administered either transcutaneously, such as via dry patches, transdermally, intramuscularly, orally in milk or other solutions, transcutaneously or nasally.
 b. Subsequent to a priming dose, 2 to 4 boosting doses are also administered by similar routes with a unit dose of 50 μg to 1 mg of immunogen.

An alternative vaccine approach is the administration of a DNA construct, capable of expressing the chimera polypeptides inserted into live attenuated bacterial vectors. Examples of potential vectors include, but are not limited to, members of the genus *Vibrio* including *Vibrio cholerae, Escherichia coli*, members of the genus *Camplyobacter*, members of the genus *Salmonella*, and members of the genus *Shigella*.

EXAMPLE 4

DscCfaE-CTA-2/CTB Chimera Scale Up

In order to produce adequate quantities of adhesin/toxin chimera, the development of a production and purification regimen is disclosed. An example is presented of a preferred production and purification procedure, although other methods can be utilized that ultimately yield stable and immunogenic adhesin/toxin chimeric product.

Figure 7:
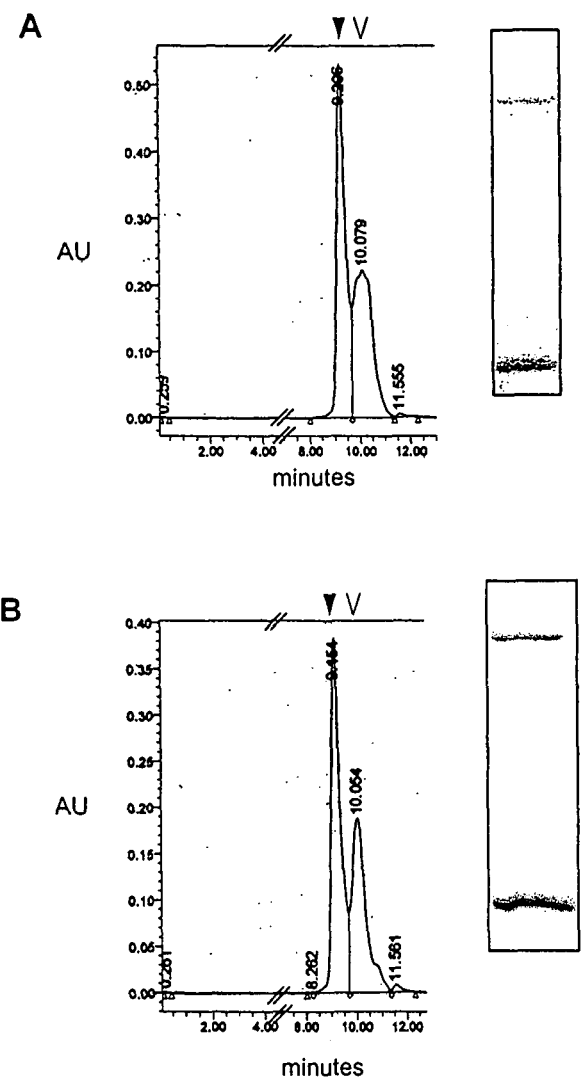

In this example, the arabinose-inducible vector (p0809C3) was selected and used to transform the *E. coli* strain BL21, which is Lon and OmpT protease deficient. Starting with 30 g of cell paste, cells were broken using microfluidization. The soluble fraction was subjected to the two step process of Talon resin chromatography and gel filtration by FPLC. After loading and washing the Talon resin, the chimera fraction was eluted with 50 mM imidazole. Referring to FIG. 7, the eluted fractions under the peak were pooled, concentrated and subjected to gel filtration. The gel filtration elution showed a two-hump peak pattern with the two peaks corresponding to chimera (early peak) and a CTB pentamer (late peak) of similar heights. The pooled chimera fractions were analyzed by SDS polyacrylamide gel electrophoresis (PAGE) and Western blot analysis with anti-CTB, anti-CTA and anti-CfaE antiserum.

In order to confirm the functional integrity of the product, the product was tested for its ability to bind to ganglioside GM-1 as illustrated in FIG. 8. ELISA assay was conducted using GM1 immobilized in wells of microtiter plates. In the assay, dscCfaE-CTA2/CTB was exposed to the GM1 immobilized plates and the bound chimera visualized by anti-CfaE antisera. No anti-CfaE reactivity was observed in control experiments when CTB or dscCfaE was allowed to interact with immobilized GM1 in the microtiter plates before probing for bound CfaE antigen with anti-CfaE antiserum. In FIG. 8 a dose response was observed over a chimera concentration range of 0.25 to 2 μg/ml added to GM 1-containing wells. The yield of chimera using this procedure was on the order of 0.05 mg/g of starting cell paste.

REFERENCES

1. Ahren, C. M., and A. M. Svennerholm. 1982. Synergistic protective effect of antibodies against *Escherichia coli* enterotoxin and colonization factor antigens. Infect. Immun. 38:74-79.

2. Altboum, Z., M. M. Levine, J. E. Galen, and E. M. Barry. 2003. Genetic characterization and immunogenicity of coli surface antigen 4 from enterotoxigenic *Escherichia coli* when it is expressed in a *Shigella* live-vector strain. Infect. Immun. 71:1352-1360.
3. Anantha, Ravi P., A. L. McVeigh, L. H. Lee, M. K. Agnew, F. J. Cassels, D. A. Scott, T S. Whittam, and S. J. Savarino. 2004. Evolutionary and functional Relationships of colonization factor antigen I and other Class 5 adhesive fimbriae of enterotoxigenic *Escherichia coli*. Inf and Imm. 72: 7190-7201.
4. Barnhart M M, Pinkner J S, Soto G E, et al. From the cover: PapD-like chaperones provide the missing information for folding of pilin proteins. Proc. Natl. Acad. Sci. U.S.A. 2000; 97:7709-14.
5. Barry, E. M., Z. Altboum, G. Losonsky, and M. M. Levine. 2003. Immune responses elicited against multiple enterotoxigenic *Escherichia coli* fimbriae and mutant LT expressed in attenuated *Shigella* vaccine strains. Vaccine 17:333-340.
6. Buhler, T., H. Hoschutzky, and K. Jann. 1991. Analysis of colonization factor antigen I, an adhesin of enterotoxigenic *Escherichia coli* O78:H11: fimbrial morphology and location of the receptor-binding site. Infect Immun 59:3876-3882.
7. Black, R. E. 1990. Epidemiology of travelers' diarrhea and relative importance of various pathogens. Rev Infect Dis 12 (Suppl 1):S73-S79.
8. Choudhury D, A. Thompson, V. Stojanoff, et al. X-ray structure of the FimC-FimH chaperone-adhesin complex from uropathogenic *Escherichia coli*. Science 1999; 285: 1061-6.
9. Clemens, J. D., D. A. Sack, J. R. Harris, J. Charkraborty, P. K. Neogy, B. Stanton, N. Huda, M. U. Khan, B. A. Kay, M. R. Khan, M. Anasaruzzaman, M. Yunus, M. R. Rao, A. M. Svennerholm, and J. Holmgren. 1988. Cross-protection by B subunit whole cell cholera vaccine against diarrhea associated with heat-labile toxin producing enterotoxigenic *Escherichia coli* results of a large-scale field trial. J. Infect. Dis. 158:372-377.
10. Dertzbaugh, M. T., and L. M. Cox. 1998. The affinity of cholera toxin for Ni2+ ion. Protein Eng. 11:577-581.
11. Domenighini, M., M. Pizza, M. G. Jobling, R. K. Holmes, and R. Rappuloli. 1995. Identification of errors among database sequence entries and comparison of correct amino acid sequences for the heat-labile enterotoxins of *Escherichia coli* and *Vibrio cholerae*. Mol Microbiol 15: 1165-1-167.
12. Evans, D. G., R. P. Silver, D. J. Evans, Jr., D. G. Chase, and S. L. Gorbach. 1975. Plasmid-controlled colonization factor associated with virulence in *Esherichia colienterotoxigenic* for humans. Infect Immun 12:656-667.
13. Froehlich, B. J., A. Karakashian, L. R. Melsen, J. C. Wakefield, and J. R. Scott. 1994. CooC and CooD are required for assembly of CS1 pili. Mol Microbiol 12:387 401.
14. Froehlich, B. J., A. Karakashian, H. Sakellaris, and J. R. Scott. 1995. Genes for CS2 pili of enterotoxigenic *Escherichia coli* and their interchangeability with those for CS 1 pili. Infect Immun 63:4849-56.
15. Gaastra, W., H. Sommerfelt, L. van Dijk, J. G. Kusters, A. M. Svennerholm, and H. M. Grewal. 2002. Antigenic variation within the subunit protein of members of the colonization factor antigen I group of fimbrial proteins in human enterotoxigenic *Escherichia coli*. Int J Med Microbiol 292:43-50.
16. Gaastra, W., and A. M. Svennerholm. 1996. Colonization factors of human enterotoxigenic *Escherichia coli* (ETEC). Trends Microbiol 4:444-452.
17. Grewal, H. M., H. Valvatne, M. K. Bhan, L. van Dijk, W. Gaastra, and H. Sommerfelt. 1997. A new putative fimbrial colonization factor, CS19, of human enterotoxigenic *Escherichia coli*. Infect Immun 65:507-513.
18. Hirst,k T.R. 1999. Cholera toxin and *Escherichia coli* heat-labile enterotoxin, p. 104-129. In E. Alouf and J. H. Freer (ed.), The Comprehensive Sourcebook of Bacterial Protein Toxins, 2 ed, vol. 6. Academic Press, San Diego.
19. Holmgren, J., and C. Czerkinsky. 2005. Muscosal immunity and vaccines. Nat. Med. 11:S45-53.
20. Holmes, R.K. 1997. Heat-labile enterotoxins (*Escherichia coli*), p. 30-33. InR. Rappuloi and C. Montecucco (ed.), Guidebook to Protein Toxins and Their use in Cell Biology. Oxford University Press, New York.
21. Huilan, S., L. G. Zhen, M. M. Mathan, M. M. Mathew, J. Olarte, R. Espejo, U. Khin Maung, M. A.Ghafoor, M. A. Khan, Z. Sami, and et al. 1991. Etiology of acute diarrhoea among children in developing countries: a multicentre study in five countries. Bull World Health Organ 69:549-55.
22. Hung, D.L., S.D. Knight, R.M. Woods, J.S. Pinkner and S.J. Hultgren. 1996. Molecular basis of two subfamilies of immunoglobulin-like chaperones. EMBO J. 15:3792-3805.
23. Jobling, M.G., and R.K. Holmes. 2005. Activation of second messenger pathways by ADP-ribosylation of G-proteins, p. 9-46. In T. Proft (ed.), Microbial Toxins: Molecular and Cellular Biology. Horizon Bioscience, Wymondham, United Kingdom.
24. Jordi, B. J. A. M., G. A. Willshaw, A. M. van der Zeijst, and W. Gaastra. 1992. The complete nucleotide sequence of region 1 of the CFA/I fimbrial operon of human enterotoxigenic *Escherichia coli*. DNA Seq 2:257-26.
25. Khalil, S. B., F. J. Cassels, H. I. Shaheen, L. K. Pannell, K. A. Kamal, B. T. Pittner, M. Mansour, R. Frenck, S. J. Savarino, and P. L. F. 2000. Presented at the 100th General Meeting of the American Society for Microbiology, Los Angeles, CA.
26. Krasan GP, Sauer FG, Cutter D, et al. Evidence for donor strand complementation in the biogenesis of Haemophilus influenzae haemagglutinating pili. Mol. Microbiol. 2000; 35:1335-47.
27. Kuehn MJ, J. Heuser, S. Normark and S.J. Hultgren. 1992. P pili in uropathogenic *E. coli* are composite fibres with distinct fibrillar adhesive tips. Nature 356:252-5.
28. Levine, M.M., R.E. Black, M.L. Clements, C.R. Young, C.P. Cheney, and P. Schad. 1984. Prevention of enterotoxigenic *Escherichia coli* diarrrheal infectin in man by vaccines that stimulate anti-adhesion (anti-pili) immunity, p223-244. In E.C. Boedeker (ed.), Attachement of Microorganisms to the Gastrointestinal Mucosal Surface. CRC Press, Boca Raton.
29. Li, X., J.L. Erbe, C.V. Lockatell, D.E. Johnson, M.G. Jobling, R.K. Holmes, and H.L. Mobley. 2004. Use of translational fusion of the MrpH fimrial adhesin-binding domain with the cholera toxin A2domain, coexpressed with the cholera toxin B subunit, as an intranasal vaccine to prevent experimental urinary tract infection by Proteus mirabilis. Infect. Immun. 72:7306-7310.
30. Low, D., B. Braaten, and M. Van der Woude. 1996. Fimbriae, p. 146-157. In F. C. Neidhardt, R. Curtiss III, J. L. Ingraham, E. C. C. Lin, K. B. Low, B. Magasanik, W.S. Reznikoff, M. Riley, M. Schaechter, and H. E. Umbarger (ed.), *Escherichia coli* and Salmonella: Cellular and Molecular Biology, 2nd ed, vol. Volume 1. ASM Press, Washington, D. C.
31. Nataro, J. P., and J. B. Kaper. 1998. Diarrheagenic *Escherichia coli*. Clin Microbiol Rev 11:142-201.
32. Perez-Casal, J., J. S. Swartley, and J. R. Scott. 1990. Gene encoding the major subunit of CS 1 pili of human enterotoxigenic *Escherichia coli*. Infect Immun 58:3594-3600.
33. Peltola, H., A. Siitonen, H. Kyronseppa, I. Simula, L. Mattila, P. Oksanen, M.J. Kataja, and M. Cadoz. 1991. Prevention of traveller's diarrhoea by oral B-subunit/whole-cell cholera vaccine. Lancet 338:1285-1289.
34. Qadri, F., A.M. Svennerholm, A.S. Faruque, and R.B. Sack. 2005. Enterotoxigenic Escherichia coli in developing countries: Epidemiology, microbiology, clinical features, treatment, and prevention. Clin. Microbiol. Rev 18:465-483.
35. Ramer, S. W., G. K. Schoolnik, C. Y. Wu, J. Hwang, S. A. Schmidt, and D. Bieber. 2002. The Type IV pilus assembly complex: Biogenic interactions among the bundle forming pilus proteins of enteropathogenic *Escherichia coli*. J Bacteriol 184:3457-65.
36. Rao, M.R., T.F. Wierzba, S.J. Savarino, R. Abu-Elyazeed, N.E1-Ghoreb, E.R. Hall, A. Naficy, I Abdel-Messih, R.W. Frenck, Jr., A.M. Svennerholm, and J.D. Clemens. 2005. Serologic correlates of protection against enterotoxigenic *Escherichia coli* diarrhea. J. Infect. Dis. 1991:562-570.
37. Savarino, S.J., E.R. Hall, S. Bassily, F.M. Brown, F. Youssef, T.F. Wierzba, L. Peruski, N.A. El-Masry, M. Safwat, M. Rao, H. El Mohamady, R. Abu-elyazeed, A. Naficy, A.M. Svennerholm, M. Jertborn, Y.J. Lee, and J.D. Clemens. 1999. Oral, inactivated, whole cell enterotoxigenic *Escherichia coli* plus cholera toxin B subunit vaccine: results of the initial evaluation in children. PRIDE Study Group. J. Infect. Dis. 179:107-114.
38. Savarino, S.J., R. Abu-Elyazeed, M.R. Rao, R.W. Frenck, I. Abdel-Messih, H.E.R., S. Putnam, H. El-Mohamady, T. Wierzba, B. Pittner, K. Kamal, P. Moyer, M.B.Z., A.M. Svennerholm, Y.J. Lee, and J.D. Clemens. 2003. Presented at the Sixth Annual Conference on Vaccine Research, Arlington, VA.
39. Sakellaris, H., and J. R. Scott. 1998. New tools in an old trade: CS1 pilus morphogenesis. Mol Microbiol 30:681-7.
40. Sakellaris, H., V. R. Penumalli, and J. R. Scott. 1999. The level of expression of the minor pilin subunit, CooD, determines the number of CS1 pili assembled on the cell surface of *Escherichia coli*. J Bacteriol 181:1694-7.
41. Sakellaris, H., G. P. Munson, and J. R. Scott. 1999. A conserved residue in the tip proteins of CS1 and CFA/I pili of enterotoxigenic *Escherichia coli* that is essential for adherence. Proc Natl Acad Sci, USA 96:12828-12832.
42. Sauer FG, K. Futterer, J.S. Pinkner, K.W. Dodson, S.J. Hultgren and G. Waksman. 1999. Structural basis of chaperone function and pilus biogenesis. Science 285:1058-61.
43. Schulz, S., M.J. Lopez, M. Kuhn, and D.L. Garbers. 1997. Disruption of the guanylyl cyclase-C gene leads to a paradoxical phenotype of viable but heat-stable enterotoxin-resistant mice. J. Clin. Invest. 100:1590-1595.
44. Scott, J. R., J. C. Wakefield, P. W. Russell, P. E. Orndorff, and B. J.Froehlich.1992. CooB is required for assembly but not transport of CS1 pilin. Mol Microbiol 6:293-300.
45. Soto, G. E., and S. J. Hultgren. 1999. Bacterial adhesins: common themes and variations in architecture and assembly. J Bacteriol 181:1059-1071.
46. Spangler, B.D. 1992. Structure and function of cholera toxin and the related *Escherichia coli* heat-labile enterotoxin. Microbiol. Rev. 56:622-647.
47. Svennerholm, A.M., C. Ahren, and M. Jertbom. 1997. Oral inactivated vaccines against enterotoxigenic *Escherichia coli*, p. 865-874. In M.M. Levine, G.C. Woodrow, J.B. Kaper, and G.S. Gabon (ed.), New Generation Vaccines, II ed. Marcel Dekker, Inc., New York.
48. Tinker, J.K., J.L. Erbe, and R.K. Holmes. 2005. Characterization of fluorescent chimeras of cholera toxin and *Escherichia coli* heat-labile enterotoxins produced by use of the twin arginine translocation system. Infect. Immun. 73:3627-3635.
49. Turner, A.K., T.D. Terry, D.A. Sack, P. Londono-Arcila, and M.J. Darsley. 2001. Construction and characterization of genetically defined aro omp mutants of enterotoxigenic *Escherichia coli* and preliminary studies of safety and immunogencity in humans. Infect. Immun. 69:4969-4979.
50. Viboud, G. I., M. M. McConnell, A. Helander, and A. M. Svennerholm. 1996. Binding of enterotoxigenic *Escherichia coli* expressing different colonization factors to tissue-cultured Caco-2 cells and to isolated human enterocytes. Microb Pathogen 21:139 147.
51. Zavialov AV, Kersley J, Korpela T, Zav'yalov VP, MacIntyre S and Knight SD. Donor strand complementation mechanism in the biogenesis of non-pilus systems. Mol. Microbiol. 2002; 45:983-995.
52. Zavialov, A.V., J. Berglund, A.F. Pudney, et al., 2003. Structure and biogenesis of the capsular F1 antigen from Yersinia pestis: preserved folding energy drives fiber formation. Cell 113:587-596.

Having described the invention, one of skill in the art will appreciate in the appended claims that many modifications and variations of the present invention are possible in light of the above teachings. It is therefore, to be understood that, within the scope of the appended claims, the invention may be practiced otherwise than as specifically described.

What is claimed is:

1. An immunogenic composition comprising a purified fusion protein, the fusion protein containing an *E. coli* minor fimbrial adhesin polypeptide or monomer, wherein the fimbrial adhesin polypeptide or monomer is derived from Class 5 fimbriae or CS3 fimbriae and is operatively connected, directly or via a linker and donor strand polypeptide, to a toxin A subunit polypeptide.

2. The immunogenic composition of claim 1, wherein the fimbrial adhesin polypeptide or monomer is operatively connected to the toxin A subunit polypeptide via a linker and donor strand polypeptide, wherein the fimbrial adhesin polypeptide or monomer is connected at its C-terminus to the linker, the linker is connected at its C-terminus to the donor strand, and the donor strand is connected at its C-terminus to the toxin A subunit.

3. The immunogenic composition of claim 1, wherein the fusion protein is noncovalently linked to a toxin B subunit.

4. The immunogenic composition of claim 1, wherein the toxin A subunit is selected from the group consisting of cholera toxin A; cholera toxin A2; *E. coli* heat-labile toxin A and *E. coli* heat-labile toxin A2.

5. The immunogenic composition of claim 1, wherein the *E. coli* fimbrial adhesin polypeptide or monomer is selected from the group consisting of colonization factor antigen I; CS4; CS14; CS1; PCF071; CS17; CS19; CS2 and CS3.

6. The immunogenic composition of claim 5, wherein the *E. coli* fimbrial adhesin polypeptide or monomer is selected from the group consisting of CfaE, CsfD, CsuD, CooD, CosD, CsdD, CsbD, CotD, and CstH.

7. The immunogenic composition of claim 1, wherein the *E. coli* fimbrial adhesin polypeptide is a monomer or a polymer of adhesin polypeptides.

8. The immunogenic composition of claim 6, wherein the *E. coli* fimbrial adhesin polypeptide or monomer has the sequence of SEQ ID NO: 4.

9. The immunogenic composition of claim 1, wherein the linker has an amino acid sequence selected from the group consisting of SEQ ID No. 1; SEQ ID No. 2 and SEQ ID No. 3.

10. The immunogenic composition of claim 1, wherein the donor strand has the amino acid sequence of SEQ ID No. 5.

11. The immunogenic composition of claim 1, wherein the donor strand is an 8 to 20 amino acid polypeptide from *E. coli* fimbrial major subunit or adhesin monomer selected from the group consisting of CfaB; CsfA; CsuA1; CsuA2; CooA; CosA; CsbA; CsdA; CotA and CstH.

12. The immunogenic composition of claim 1, wherein the fusion protein contains a histidine tag operatively linked to the C-terminus of the donor strand and to the N-terminus of the toxin A subunit polypeptide.

13. The immunogenic composition of claim 1, wherein the fusion protein comprises a polypeptide having a sequence selected from the group consisting of SEQ ID No. 6; SEQ ID No. 7; SEQ ID No. 9; SEQ ID No. 10; SEQ ID No. 11; SEQ ID No. 12; SEQ ID No. 13; SEQ ID No. 15; SEQ ID No. 16 and SEQ ID No. 30.

14. The immunogenic composition of claim 1, wherein the toxin A subunit has the sequence of SEQ ID No. 18 or SEQ ID No. 19.

15. The immunogenic composition of claim 3, wherein the fusion protein or the toxin B subunit is operatively connected at its N-terminus to a signal sequence.

16. The immunogenic composition of claim 3, wherein the toxin B subunit is cholera toxin B or *E. coli* heat-labile toxin B.

17. The immunogenic composition of claim 3, wherein the fusion protein and the toxin B subunit are expressed from a single expression vector.

18. The immunogenic composition of claim 3, wherein the toxin B subunit has a sequence selected from the group consisting of SEQ ID No. 20; SEQ ID No. 21; SEQ ID No. 22 and SEQ ID No. 23.

19. The immunogenic composition of claim 15, wherein the signal sequence is the LTIIb toxin signal sequence of SEQ ID No. 24.

20. A method of inducing an immune response comprising the steps:
  a) administering a priming dose of the composition of claim 1; and
  b) administering boosting doses, with a first dose at least 1 week after the priming dose, with a unit dose range of 50 µg to 1 mg of the immunogenic composition in a buffered aqueous solution, wherein an immune response is elicited.

21. The method of claim 20, wherein the fusion protein is noncovalently linked to a toxin B subunit.

22. The method of claim 20, wherein the E. coli fimbrial adhesin polypeptide or monomer is selected from the group consisting of CfaE; CsfD; CsuD; CooD; CosD; CsdD; CsbD; CotD and CstH.

23. The method of claim 20, wherein the fimbrial adhesin polypeptide or monomer is operatively connected to the toxin A subunit polypeptide via a linker and donor strand polypeptide, wherein the fimbrial adhesin polypeptide or monomer is connected at its C-terminus to the linker, the linker is connected at its C-terminus to the donor strand, and the donor strand is connected at its C-terminus to the toxin A subunit.

24. The method of claim 20, wherein the E. coli fimbrial adhesin polypeptide is a monomer or a polymer of adhesin polypeptides.

25. The method of claim 20, wherein the fusion protein comprises a polypeptide having a sequence selected from the group consisting of SEQ ID No. 6; SEQ ID No. 7; SEQ ID No. 9; SEQ ID No. 10; SEQ ID No. 11; SEQ ID No. 12; SEQ ID No. 13; SEQ ID No. 15; SEQ ID No. 16 and SEQ ID No. 30.

26. The method of claim 20, wherein the toxin A subunit is selected from the group consisting of cholera toxin A; cholera toxin A2; E. coli heat-labile toxin A and E. coli heat-labile toxin A2.

27. The method of claim 20, wherein the toxin A subunit has the sequence of SEQ ID No. 18 or SEQ ID No. 19.

28. The method of claim 20, wherein the immune response inhibits enterotoxigenic E. coli fimbriae adherence to human cells.

29. The method of claim 20, wherein the immune response reduces or prevents diarrhea in humans.

30. The method of claim 20, wherein the composition is administered subcutaneously, transdermally, intramuscularly, orally, transcutaneously or nasally.

31. The method of claim 20, wherein the fusion protein is produced by a DNA expression system in a live attenuated bacterial vector prior to administration.

32. The method of claim 21, wherein the toxin B subunit has a sequence selected from the group consisting of SEQ ID No. 20; SEQ ID No. 21; SEQ ID No. 22 and SEQ ID No. 23.

33. The method of claim 21, wherein the composition is administered subcutaneously, transdermally, intramuscularly, orally, transcutaneously or nasally.

34. The method of claim 21, wherein the fusion protein is produced by a DNA expression system in a live attenuated bacterial vector prior to administration.

35. The method of claim 21, wherein the immune response inhibits enterotoxigenic E. coli fimbriae adherence to human cells.

36. The method of claim 21, wherein the immune response reduces or prevents diarrhea in humans.

37. The method of claim 23, wherein the donor strand is an 8 to 20 amino acid polypeptide from E. coli fimbrial major subunit or adhesin monomer selected from the group consisting of CfaB; CsfA; CsuA1; CsuA2; CooA; CosA; CsbA; CsdA; CotA and CstH.

38. The method of claim 30, wherein the composition is administered orally by solution or enteric coated granule capsule.

39. The method of claim 30, wherein the composition is administered transcutaneously by a dry patch.

40. The method of claim 31, wherein the bacterial vector is derived from a bacterium selected from the group consisting of E. coli, member of the genus Shigella, member of the genus Camplylobacter, member of the genus Salmonella, and member of the genus Vibrio.

41. The method of claim 33, wherein the composition is administered orally by solution or enteric coated granule capsule.

42. The method of claim 33, wherein the composition is administered transcutaneously by a dry patch.

43. The method of claim 34, wherein the bacterial vector is derived from a bacterium selected from the group consisting of E. coli, member of the genus Shigella, member of the genus Camplylobacter, member of the genus Salmonella, and member of the genus Vibrio.

* * * * *

SEQUENCE LISTING

```
<160> NUMBER OF SEQ ID NOS: 35

<210> SEQ ID NO 1
<211> LENGTH: 4
<212> TYPE: PRT
<213> ORGANISM: Escherichia coli

<400> SEQUENCE: 1

Asp Asn Lys Gln
1
```

```
<210> SEQ ID NO 2
<211> LENGTH: 5
<212> TYPE: PRT
<213> ORGANISM: Escherichia coli

<400> SEQUENCE: 2

Gly Asp Asn Lys Gln
1               5

<210> SEQ ID NO 3
<211> LENGTH: 6
<212> TYPE: PRT
<213> ORGANISM: Escherichia coli

<400> SEQUENCE: 3

Gly Asp Asn Lys Gln Gly
1               5

<210> SEQ ID NO 4
<211> LENGTH: 360
<212> TYPE: PRT
<213> ORGANISM: Escherichia coli

<400> SEQUENCE: 4

Met Asn Lys Ile Leu Phe Ile Phe Thr Leu Phe Ser Ser Gly Phe
1               5                   10                  15

Phe Thr Phe Ala Val Ser Ala Asp Lys Asn Pro Gly Ser Glu Asn Met
                20                  25                  30

Thr Asn Thr Ile Gly Pro His Asp Arg Gly Gly Ser Ser Pro Ile Tyr
            35                  40                  45

Asn Ile Leu Asn Ser Tyr Leu Thr Ala Tyr Asn Gly Ser His His Leu
    50                  55                  60

Tyr Asp Arg Met Ser Phe Leu Cys Leu Ser Ser Gln Asn Thr Leu Asn
65                  70                  75                  80

Gly Ala Cys Pro Ser Ser Asp Ala Pro Gly Thr Ala Thr Ile Asp Gly
                85                  90                  95

Glu Thr Asn Ile Thr Leu Gln Phe Thr Glu Lys Arg Ser Leu Ile Lys
            100                 105                 110

Arg Glu Leu Gln Ile Lys Gly Tyr Lys Gln Phe Leu Phe Lys Asn Ala
        115                 120                 125

Asn Cys Pro Ser Lys Leu Ala Leu Asn Ser Ser His Phe Gln Cys Asn
    130                 135                 140

Arg Glu Gln Ala Ser Gly Ala Thr Leu Ser Leu Tyr Ile Pro Ala Gly
145                 150                 155                 160

Glu Leu Asn Lys Leu Pro Phe Gly Gly Val Trp Asn Ala Val Leu Lys
                165                 170                 175

Leu Asn Val Lys Arg Arg Tyr Asp Thr Thr Tyr Gly Tyr Thr Ile
            180                 185                 190

Asn Ile Thr Val Asn Leu Thr Asp Lys Gly Asn Ile Gln Ile Trp Leu
        195                 200                 205

Pro Gln Phe Lys Ser Asn Ala Arg Val Asp Leu Asn Leu Arg Pro Thr
    210                 215                 220

Gly Gly Gly Thr Tyr Ile Gly Arg Asn Ser Val Asp Met Cys Phe Tyr
225                 230                 235                 240

Asp Gly Tyr Ser Thr Asn Ser Ser Leu Glu Ile Arg Phe Gln Asp
                245                 250                 255

Asp Asn Ser Lys Ser Asp Gly Lys Phe Tyr Leu Lys Lys Ile Asn Asp
            260                 265                 270
```

```
Asp Ser Lys Glu Leu Val Tyr Thr Leu Ser Leu Leu Ala Gly Lys
        275                 280                 285

Asn Leu Thr Pro Thr Asn Gly Gln Ala Leu Asn Ile Asn Thr Ala Ser
290                 295                 300

Leu Glu Thr Asn Trp Asn Arg Ile Thr Ala Val Thr Met Pro Glu Ile
305                 310                 315                 320

Ser Val Pro Val Leu Cys Trp Pro Gly Arg Leu Gln Leu Asp Ala Lys
                325                 330                 335

Val Lys Asn Pro Glu Ala Gly Gln Tyr Met Gly Asn Ile Lys Ile Thr
                340                 345                 350

Phe Thr Pro Ser Ser Gln Thr Leu
                355                 360

<210> SEQ ID NO 5
<211> LENGTH: 20
<212> TYPE: PRT
<213> ORGANISM: Escherichia coli

<400> SEQUENCE: 5

Val Glu Lys Asn Ile Thr Val Thr Ala Ser Val Asp Pro Val Ile Asp
1               5                   10                  15

Leu Leu Gln Ala
            20

<210> SEQ ID NO 6
<211> LENGTH: 360
<212> TYPE: PRT
<213> ORGANISM: Escherichia coli

<400> SEQUENCE: 6

Asp Lys Asn Pro Gly Ser Glu Asn Met Thr Asn Thr Ile Gly Pro His
1               5                   10                  15

Asp Arg Gly Gly Ser Ser Pro Ile Tyr Asn Ile Leu Asn Ser Tyr Leu
                20                  25                  30

Thr Ala Tyr Asn Gly Ser His His Leu Tyr Asp Arg Met Ser Phe Leu
            35                  40                  45

Cys Leu Ser Ser Gln Asn Thr Leu Asn Gly Ala Cys Pro Ser Ser Asp
50                  55                  60

Ala Pro Gly Thr Ala Thr Ile Asp Gly Glu Thr Asn Ile Thr Leu Gln
65                  70                  75                  80

Phe Thr Glu Lys Arg Ser Leu Ile Lys Arg Glu Leu Gln Ile Lys Gly
                85                  90                  95

Tyr Lys Gln Phe Leu Phe Lys Asn Ala Asn Cys Pro Ser Lys Leu Ala
                100                 105                 110

Leu Asn Ser Ser His Phe Gln Cys Asn Arg Glu Gln Ala Ser Gly Ala
            115                 120                 125

Thr Leu Ser Leu Tyr Ile Pro Ala Gly Glu Leu Asn Lys Leu Pro Phe
130                 135                 140

Gly Gly Val Trp Asn Ala Val Leu Lys Leu Asn Val Lys Arg Arg Tyr
145                 150                 155                 160

Asp Thr Thr Tyr Gly Thr Tyr Thr Ile Asn Ile Thr Val Asn Leu Thr
                165                 170                 175

Asp Lys Gly Asn Ile Gln Ile Trp Leu Pro Gln Phe Lys Ser Asn Ala
            180                 185                 190

Arg Val Asp Leu Asn Leu Arg Pro Thr Gly Gly Gly Thr Tyr Ile Gly
        195                 200                 205
```

```
Arg Asn Ser Val Asp Met Cys Phe Tyr Asp Gly Tyr Ser Thr Asn Ser
    210                 215                 220

Ser Ser Leu Glu Ile Arg Phe Gln Asp Asp Asn Ser Lys Ser Asp Gly
225                 230                 235                 240

Lys Phe Tyr Leu Lys Lys Ile Asn Asp Asp Ser Lys Glu Leu Val Tyr
                245                 250                 255

Thr Leu Ser Leu Leu Leu Ala Gly Lys Asn Leu Thr Pro Thr Asn Gly
            260                 265                 270

Gln Ala Leu Asn Ile Asn Thr Ala Ser Leu Glu Thr Asn Trp Asn Arg
        275                 280                 285

Ile Thr Ala Val Thr Met Pro Glu Ile Ser Val Pro Val Leu Cys Trp
    290                 295                 300

Pro Gly Arg Leu Gln Leu Asp Ala Lys Val Lys Asn Pro Glu Ala Gly
305                 310                 315                 320

Gln Tyr Met Gly Asn Ile Lys Ile Thr Phe Thr Pro Ser Ser Gln Thr
                325                 330                 335

Leu Asp Asn Lys Gln Val Glu Lys Asn Ile Thr Val Thr Ala Ser Val
            340                 345                 350

Asp Pro Val Ile Asp Leu Leu Gln
            355                 360

<210> SEQ ID NO 7
<211> LENGTH: 181
<212> TYPE: PRT
<213> ORGANISM: Escherichia coli

<400> SEQUENCE: 7

Asp Lys Asn Pro Gly Ser Glu Asn Met Thr Asn Thr Ile Gly Pro His
1               5                   10                  15

Asp Arg Gly Gly Ser Ser Pro Ile Tyr Asn Ile Leu Asn Ser Tyr Leu
                20                  25                  30

Thr Ala Tyr Asn Gly Ser His His Leu Tyr Asp Arg Met Ser Phe Leu
            35                  40                  45

Cys Leu Ser Ser Gln Asn Thr Leu Asn Gly Ala Cys Pro Ser Ser Asp
50                  55                  60

Ala Pro Gly Thr Ala Thr Ile Asp Gly Glu Thr Asn Ile Thr Leu Gln
65                  70                  75                  80

Phe Thr Glu Lys Arg Ser Leu Ile Lys Arg Glu Leu Gln Ile Lys Gly
                85                  90                  95

Tyr Lys Gln Phe Leu Phe Lys Asn Ala Asn Cys Pro Ser Lys Leu Ala
            100                 105                 110

Leu Asn Ser Ser His Phe Gln Cys Asn Arg Glu Gln Ala Ser Gly Ala
        115                 120                 125

Thr Leu Ser Leu Tyr Ile Pro Ala Gly Glu Leu Asn Lys Leu Pro Phe
    130                 135                 140

Gly Gly Val Trp Asn Ala Val Leu Lys Leu Asn Val Lys Arg Arg Tyr
145                 150                 155                 160

Asp Thr Thr Tyr Gly Thr Tyr Thr Ile Asn Ile Thr Val Asn Leu Thr
                165                 170                 175

Asp Lys Gly Asn Ile
            180

<210> SEQ ID NO 8
<211> LENGTH: 23
<212> TYPE: PRT
```

<213> ORGANISM: Escherichia coli

<400> SEQUENCE: 8

```
Met Ser Phe Lys Lys Ile Ile Lys Ala Phe Val Ile Met Ala Ala Leu
1               5                   10                  15

Val Ser Val Gln Ala His Ala
            20
```

<210> SEQ ID NO 9
<211> LENGTH: 360
<212> TYPE: PRT
<213> ORGANISM: Escherichia coli

<400> SEQUENCE: 9

```
Asp Lys Asn Pro Gly Ser Glu Asn Met Thr Asn Thr Ile Gly Pro His
1               5                   10                  15

Asp Arg Gly Gly Ser Ser Pro Ile Tyr Asn Ile Leu Asn Ser Tyr Leu
            20                  25                  30

Thr Ala Tyr Asn Gly Ser His His Leu Tyr Asp Arg Met Ser Phe Leu
        35                  40                  45

Cys Leu Ser Ser Gln Asn Thr Leu Asn Gly Ala Cys Pro Ser Ser Asp
    50                  55                  60

Ala Pro Gly Thr Ala Thr Ile Asp Gly Glu Thr Asn Ile Thr Leu Gln
65                  70                  75                  80

Phe Thr Glu Lys Arg Ser Leu Ile Lys Arg Glu Leu Gln Ile Lys Gly
                85                  90                  95

Tyr Lys Gln Phe Leu Phe Lys Asn Ala Asn Cys Pro Ser Lys Leu Ala
            100                 105                 110

Leu Asn Ser Ser His Phe Gln Cys Asn Arg Glu Gln Ala Ser Gly Ala
        115                 120                 125

Thr Leu Ser Leu Tyr Ile Pro Ala Gly Glu Leu Asn Lys Leu Pro Phe
    130                 135                 140

Gly Gly Val Trp Asn Ala Val Leu Lys Leu Asn Val Lys Arg Arg Tyr
145                 150                 155                 160

Asp Thr Thr Tyr Gly Thr Tyr Thr Ile Asn Ile Thr Val Asn Leu Thr
                165                 170                 175

Asp Lys Gly Asn Ile Gln Ile Trp Leu Pro Gln Phe Lys Ser Asn Ala
            180                 185                 190

Arg Val Asp Leu Asn Leu Arg Pro Thr Gly Gly Thr Tyr Ile Gly
        195                 200                 205

Arg Asn Ser Val Asp Met Cys Phe Tyr Asp Gly Tyr Ser Thr Asn Ser
    210                 215                 220

Ser Ser Leu Glu Ile Arg Phe Gln Asp Asp Asn Ser Lys Ser Asp Gly
225                 230                 235                 240

Lys Phe Tyr Leu Lys Lys Ile Asn Asp Asp Ser Lys Glu Leu Val Tyr
                245                 250                 255

Thr Leu Ser Leu Leu Leu Ala Gly Lys Asn Leu Thr Pro Thr Asn Gly
            260                 265                 270

Gln Ala Leu Asn Ile Asn Thr Ala Ser Leu Glu Thr Asn Trp Asn Arg
        275                 280                 285

Ile Thr Ala Val Thr Met Pro Glu Ile Ser Val Pro Val Leu Cys Trp
    290                 295                 300

Pro Gly Arg Leu Gln Leu Asp Ala Lys Val Asn Asn Pro Glu Ala Gly
305                 310                 315                 320

Gln Tyr Met Gly Asn Ile Lys Ile Thr Phe Thr Pro Ser Ser Gln Thr
```

```
                    325                 330                 335
Leu Asp Asn Lys Gln Val Glu Lys Asn Ile Thr Val Thr Ala Ser Val
                340                 345                 350
Asp Pro Val Ile Asp Leu Leu Gln
            355                 360

<210> SEQ ID NO 10
<211> LENGTH: 360
<212> TYPE: PRT
<213> ORGANISM: Escherichia coli

<400> SEQUENCE: 10

Asp Lys Asn Pro Gly Ser Glu Asn Met Thr Asn Thr Ile Gly Pro His
1               5                   10                  15

Asp Arg Gly Gly Ser Ser Pro Ile Tyr Asn Ile Leu Asn Ser Tyr Leu
                20                  25                  30

Thr Ala Tyr Asn Gly Ser His His Leu Tyr Asp Arg Met Ser Phe Leu
            35                  40                  45

Cys Leu Ser Ser Gln Asn Thr Leu Asn Gly Ala Cys Pro Ser Ser Asp
        50                  55                  60

Ala Pro Gly Thr Ala Thr Ile Asp Gly Glu Thr Asn Ile Thr Leu Gln
65                  70                  75                  80

Phe Thr Glu Lys Arg Ser Leu Ile Lys Arg Glu Leu Gln Ile Lys Gly
                85                  90                  95

Tyr Lys Gln Phe Leu Phe Lys Asn Ala Asn Cys Pro Ser Lys Leu Ala
                100                 105                 110

Leu Asn Ser Ser His Phe Gln Cys Asn Arg Glu Gln Ala Ser Gly Ala
            115                 120                 125

Thr Leu Ser Leu Tyr Ile Pro Ala Gly Glu Leu Asn Lys Leu Pro Phe
        130                 135                 140

Gly Gly Val Trp Asn Ala Val Leu Lys Leu Asn Val Lys Arg Arg Tyr
145                 150                 155                 160

Asp Thr Thr Tyr Gly Thr Tyr Thr Ile Asn Ile Thr Val Asn Leu Thr
                165                 170                 175

Asp Lys Gly Asn Ile Gln Ile Trp Leu Pro Gln Phe Lys Ser Asn Ala
                180                 185                 190

Arg Val Asp Leu Asn Leu Arg Pro Thr Gly Gly Gly Thr Tyr Ile Gly
            195                 200                 205

Arg Asn Ser Val Asp Met Cys Phe Tyr Asp Gly Tyr Ser Thr Asn Ser
        210                 215                 220

Ser Ser Leu Glu Ile Arg Phe Gln Asp Asp Asn Ser Lys Ser Asp Gly
225                 230                 235                 240

Lys Phe Tyr Leu Lys Lys Ile Asn Asp Asp Ser Lys Glu Leu Val Tyr
                245                 250                 255

Thr Leu Ser Leu Leu Leu Ala Gly Lys Asn Leu Thr Pro Thr Asn Gly
                260                 265                 270

Gln Ala Leu Asn Ile Asn Thr Ala Ser Leu Glu Thr Asn Trp Asn Arg
            275                 280                 285

Ile Thr Ala Val Thr Met Pro Glu Ile Ser Val Pro Val Leu Cys Trp
        290                 295                 300

Pro Gly Arg Leu Gln Leu Asp Ala Lys Val Ser Asn Pro Glu Ala Gly
305                 310                 315                 320

Gln Tyr Met Gly Asn Ile Lys Ile Thr Phe Thr Pro Ser Ser Gln Thr
                325                 330                 335
```

Leu Asp Asn Lys Gln Val Glu Lys Asn Ile Thr Val Thr Ala Ser Val
          340                 345                 350

Asp Pro Val Ile Asp Leu Leu Gln
          355                 360

<210> SEQ ID NO 11
<211> LENGTH: 383
<212> TYPE: PRT
<213> ORGANISM: Escherichia coli

<400> SEQUENCE: 11

Met Ser Phe Lys Lys Ile Ile Lys Ala Phe Val Ile Met Ala Ala Leu
1               5                   10                  15

Val Ser Val Gln Ala His Ala Asp Lys Asn Pro Gly Ser Glu Asn Met
            20                  25                  30

Thr Asn Thr Ile Gly Pro His Asp Arg Gly Gly Ser Ser Pro Ile Tyr
        35                  40                  45

Asn Ile Leu Asn Ser Tyr Leu Thr Ala Tyr Asn Gly Ser His His Leu
    50                  55                  60

Tyr Asp Arg Met Ser Phe Leu Cys Leu Ser Ser Gln Asn Thr Leu Asn
65                  70                  75                  80

Gly Ala Cys Pro Ser Ser Asp Ala Pro Gly Thr Ala Thr Ile Asp Gly
                85                  90                  95

Glu Thr Asn Ile Thr Leu Gln Phe Thr Glu Lys Arg Ser Leu Ile Lys
            100                 105                 110

Arg Glu Leu Gln Ile Lys Gly Tyr Lys Gln Phe Leu Phe Lys Asn Ala
        115                 120                 125

Asn Cys Pro Ser Lys Leu Ala Leu Asn Ser Ser His Phe Gln Cys Asn
    130                 135                 140

Arg Glu Gln Ala Ser Gly Ala Thr Leu Ser Leu Tyr Ile Pro Ala Gly
145                 150                 155                 160

Glu Leu Asn Lys Leu Pro Phe Gly Gly Val Trp Asn Ala Val Leu Lys
                165                 170                 175

Leu Asn Val Lys Arg Arg Tyr Asp Thr Thr Tyr Gly Thr Tyr Thr Ile
            180                 185                 190

Asn Ile Thr Val Asn Leu Thr Asp Lys Gly Asn Ile Gln Ile Trp Leu
        195                 200                 205

Pro Gln Phe Lys Ser Asn Ala Arg Val Asp Leu Asn Leu Arg Pro Thr
    210                 215                 220

Gly Gly Gly Thr Tyr Ile Gly Arg Asn Ser Val Asp Met Cys Phe Tyr
225                 230                 235                 240

Asp Gly Tyr Ser Thr Asn Ser Ser Ser Leu Glu Ile Arg Phe Gln Asp
                245                 250                 255

Asp Asn Ser Lys Ser Asp Gly Lys Phe Tyr Leu Lys Lys Ile Asn Asp
            260                 265                 270

Asp Ser Lys Glu Leu Val Tyr Thr Leu Ser Leu Leu Leu Ala Gly Lys
        275                 280                 285

Asn Leu Thr Pro Thr Asn Gly Gln Ala Leu Asn Ile Asn Thr Ala Ser
    290                 295                 300

Leu Glu Thr Asn Trp Asn Arg Ile Thr Ala Val Thr Met Pro Glu Ile
305                 310                 315                 320

Ser Val Pro Val Leu Cys Trp Pro Gly Arg Leu Gln Leu Asp Ala Lys
                325                 330                 335

Val Thr Asn Pro Glu Ala Gly Gln Tyr Met Gly Asn Ile Lys Ile Thr
            340                 345                 350

```
Phe Thr Pro Ser Ser Gln Thr Leu Asp Asn Lys Gln Val Glu Lys Asn
            355                 360                 365

Ile Thr Val Thr Ala Ser Val Asp Pro Val Ile Asp Leu Leu Gln
    370                 375                 380
```

<210> SEQ ID NO 12
<211> LENGTH: 368
<212> TYPE: PRT
<213> ORGANISM: Escherichia coli

<400> SEQUENCE: 12

```
Gly Arg Tyr Pro Glu Thr Thr Val Gly Asn Leu Thr Lys Ser Phe Gln
1               5                   10                  15

Ala Pro Arg Gln Asp Arg Ser Val Gln Ser Pro Ile Tyr Asn Ile Phe
            20                  25                  30

Thr Asn His Val Ala Gly Tyr Ser Leu Ser His Asn Leu Tyr Asp Arg
        35                  40                  45

Ile Val Phe Leu Cys Thr Ser Ser Asn Pro Val Asn Gly Ala Cys
    50                  55                  60

Pro Thr Leu Gly Thr Ser Gly Val Gln Tyr Gly Thr Thr Ile Thr
65                  70                  75                  80

Leu Gln Phe Thr Glu Lys Arg Ser Leu Ile Lys Arg Asn Ile Asn Leu
            85                  90                  95

Ala Gly Asn Lys Lys Pro Ile Trp Glu Asn Gln Ser Cys Asp Thr Ser
            100                 105                 110

Asn Leu Met Val Leu Asn Ser Lys Ser Trp Ser Cys Gly His Tyr Gly
        115                 120                 125

Asn Ala Asn Gly Thr Leu Leu Asn Leu Tyr Ile Pro Ala Gly Glu Ile
    130                 135                 140

Asn Lys Leu Pro Phe Gly Gly Ile Trp Glu Ala Thr Leu Ile Leu Arg
145                 150                 155                 160

Leu Ser Arg Tyr Gly Glu Val Ser Ser Thr His Tyr Gly Asn Tyr Thr
            165                 170                 175

Val Asn Ile Thr Val Asp Leu Thr Asp Lys Gly Asn Ile Gln Val Trp
        180                 185                 190

Leu Pro Gly Phe His Ser Asn Pro Arg Val Asp Leu Asn Leu His Pro
    195                 200                 205

Ile Gly Asn Tyr Lys Tyr Ser Gly Ser Asn Ser Leu Asp Met Cys Phe
    210                 215                 220

Tyr Asp Gly Tyr Ser Thr Asn Ser Asp Ser Met Val Ile Lys Phe Gln
225                 230                 235                 240

Asp Asp Asn Pro Thr Tyr Ser Ser Glu Tyr Asn Leu Tyr Lys Ile Gly
            245                 250                 255

Gly Thr Glu Lys Leu Pro Tyr Ala Val Ser Leu Leu Met Gly Glu Lys
            260                 265                 270

Ile Phe Tyr Pro Val Asn Gly Gln Ser Phe Thr Ile Asn Asp Ser Ser
    275                 280                 285

Val Leu Glu Thr Asn Trp Asn Arg Val Thr Ala Val Ala Met Pro Glu
    290                 295                 300

Val Asn Val Pro Val Leu Cys Trp Pro Ala Arg Leu Leu Leu Asn Ala
305                 310                 315                 320

Asp Val Asn Ala Pro Asp Ala Gly Gln Tyr Ser Gly Gln Ile Tyr Ile
            325                 330                 335

Thr Phe Thr Pro Ser Val Glu Asn Leu Asp Asn Lys Gln Val Glu Lys
```

```
                340               345               350
Asn Ile Thr Val Arg Ala Ser Val Asp Pro Lys Leu Asp Leu Leu Gln
        355               360               365
```

<210> SEQ ID NO 13
<211> LENGTH: 184
<212> TYPE: PRT
<213> ORGANISM: Escherichia coli

<400> SEQUENCE: 13

```
Gly Arg Tyr Pro Glu Thr Thr Val Gly Asn Leu Thr Lys Ser Phe Gln
1               5                  10                  15

Ala Pro Arg Gln Asp Arg Ser Val Gln Ser Pro Ile Tyr Asn Ile Phe
            20                  25                  30

Thr Asn His Val Ala Gly Tyr Ser Leu Ser His Asn Leu Tyr Asp Arg
        35                  40                  45

Ile Val Phe Leu Cys Thr Ser Ser Asn Pro Val Asn Gly Ala Cys
    50                  55                  60

Pro Thr Leu Gly Thr Ser Gly Val Gln Tyr Gly Thr Thr Ile Thr
65                  70                  75                  80

Leu Gln Phe Thr Glu Lys Arg Ser Leu Ile Lys Arg Asn Ile Asn Leu
                85                  90                  95

Ala Gly Asn Lys Lys Pro Ile Trp Glu Asn Gln Ser Cys Asp Thr Ser
            100                 105                 110

Asn Leu Met Val Leu Asn Ser Lys Ser Trp Ser Cys Gly His Tyr Gly
        115                 120                 125

Asn Ala Asn Gly Thr Leu Leu Asn Leu Tyr Ile Pro Ala Gly Glu Ile
    130                 135                 140

Asn Lys Leu Pro Phe Gly Gly Ile Trp Glu Ala Thr Leu Ile Leu Arg
145                 150                 155                 160

Leu Ser Arg Tyr Gly Glu Val Ser Ser Thr His Tyr Gly Asn Tyr Thr
                165                 170                 175

Val Asn Ile Thr Val Asp Leu Thr
            180
```

<210> SEQ ID NO 14
<211> LENGTH: 18
<212> TYPE: PRT
<213> ORGANISM: Escherichia coli

<400> SEQUENCE: 14

```
Met Lys Lys Ile Phe Ile Phe Leu Ser Ile Ile Phe Ser Ala Val Val
1               5                  10                  15

Ser Ala
```

<210> SEQ ID NO 15
<211> LENGTH: 368
<212> TYPE: PRT
<213> ORGANISM: Escherichia coli

<400> SEQUENCE: 15

```
Gln Ser Trp His Thr Asn Val Glu Ala Gly Ser Ile Asn Lys Thr Glu
1               5                  10                  15

Ser Ile Gly Pro Ile Asp Arg Ser Ala Ala Ser Tyr Pro Ala His
            20                  25                  30

Tyr Ile Phe His Glu His Val Ala Gly Tyr Asn Lys Asp His Ser Leu
        35                  40                  45
```

```
Phe Asp Arg Met Thr Phe Leu Cys Met Ser Ser Thr Asp Ala Ser Lys
 50                  55                  60

Gly Ala Cys Pro Thr Gly Glu Asn Ser Lys Ser Ser Gln Gly Glu Thr
 65                  70                  75                  80

Asn Ile Lys Leu Ile Phe Thr Glu Lys Lys Ser Leu Ala Arg Lys Thr
                 85                  90                  95

Leu Asn Leu Lys Gly Tyr Lys Arg Phe Leu Tyr Glu Ser Asp Arg Cys
                100                 105                 110

Ile His Tyr Val Asp Lys Met Asn Leu Asn Ser His Thr Val Lys Cys
            115                 120                 125

Val Gly Ser Phe Thr Arg Gly Val Asp Phe Thr Leu Tyr Ile Pro Gln
130                 135                 140

Gly Glu Ile Asp Gly Leu Leu Thr Gly Gly Ile Trp Glu Ala Thr Leu
145                 150                 155                 160

Glu Leu Arg Val Lys Arg His Tyr Asp Tyr Asn His Gly Thr Tyr Lys
                165                 170                 175

Val Asn Ile Thr Val Asp Leu Thr Asp Lys Gly Asn Ile Gln Val Trp
                180                 185                 190

Thr Pro Lys Phe His Ser Asp Pro Arg Ile Asp Leu Asn Leu Arg Pro
            195                 200                 205

Glu Gly Asn Gly Lys Tyr Ser Gly Ser Asn Val Leu Glu Met Cys Leu
210                 215                 220

Tyr Asp Gly Tyr Ser Thr His Ser Gln Ser Ile Glu Met Arg Phe Gln
225                 230                 235                 240

Asp Asp Ser Gln Thr Gly Asn Asn Glu Tyr Asn Leu Ile Lys Thr Gly
                245                 250                 255

Glu Pro Leu Lys Lys Leu Pro Tyr Lys Leu Ser Leu Leu Leu Gly Gly
                260                 265                 270

Arg Glu Phe Tyr Pro Asn Asn Gly Glu Ala Phe Thr Ile Asn Asp Thr
            275                 280                 285

Ser Ser Leu Phe Ile Asn Trp Asn Arg Ile Lys Ser Val Ser Leu Pro
290                 295                 300

Gln Ile Ser Ile Pro Val Leu Cys Trp Pro Ala Asn Leu Thr Phe Met
305                 310                 315                 320

Ser Glu Leu Asn Asn Pro Glu Ala Gly Glu Tyr Ser Gly Ile Leu Asn
                325                 330                 335

Val Thr Phe Thr Pro Ser Ser Ser Leu Asp Asn Lys Gln Ala Glu
                340                 345                 350

Lys Asn Ile Thr Val Thr Ala Ser Val Asp Pro Thr Ile Asp Leu Met
            355                 360                 365

<210> SEQ ID NO 16
<211> LENGTH: 184
<212> TYPE: PRT
<213> ORGANISM: Escherichia coli

<400> SEQUENCE: 16

Gln Ser Trp His Thr Asn Val Glu Ala Gly Ser Ile Asn Lys Thr Glu
 1               5                  10                  15

Ser Ile Gly Pro Ile Asp Arg Ser Ala Ala Ser Tyr Pro Ala His
                 20                  25                  30

Tyr Ile Phe His Glu His Val Ala Gly Tyr Asn Lys Asp His Ser Leu
                 35                  40                  45

Phe Asp Arg Met Thr Phe Leu Cys Met Ser Ser Thr Asp Ala Ser Lys
 50                  55                  60
```

```
Gly Ala Cys Pro Thr Gly Glu Asn Ser Lys Ser Gln Gly Glu Thr
 65                  70                  75                  80

Asn Ile Lys Leu Ile Phe Thr Glu Lys Lys Ser Leu Ala Arg Lys Thr
                 85                  90                  95

Leu Asn Leu Lys Gly Tyr Lys Arg Phe Leu Tyr Glu Ser Asp Arg Cys
            100                 105                 110

Ile His Tyr Val Asp Lys Met Asn Leu Asn Ser His Thr Val Lys Cys
            115                 120                 125

Val Gly Ser Phe Thr Arg Gly Val Asp Phe Thr Leu Tyr Ile Pro Gln
        130                 135                 140

Gly Glu Ile Asp Gly Leu Leu Thr Gly Gly Ile Trp Glu Ala Thr Leu
145                 150                 155                 160

Glu Leu Arg Val Lys Arg His Tyr Asp Tyr Asn His Gly Thr Tyr Lys
                165                 170                 175

Val Asn Ile Thr Val Asp Leu Thr
            180
```

<210> SEQ ID NO 17
<211> LENGTH: 18
<212> TYPE: PRT
<213> ORGANISM: Escherichia coli

<400> SEQUENCE: 17

```
Met Lys Lys Val Ile Phe Val Leu Ser Met Phe Leu Cys Ser Gln Val
 1               5                  10                  15

Tyr Gly
```

<210> SEQ ID NO 18
<211> LENGTH: 47
<212> TYPE: PRT
<213> ORGANISM: Escherichia coli

<400> SEQUENCE: 18

```
Ser Thr Gly Asp Thr Cys Asn Glu Glu Thr Gln Asn Leu Ser Thr Ile
 1               5                  10                  15

Tyr Leu Arg Lys Tyr Gln Ser Lys Val Lys Arg Gln Ile Phe Ser Asp
            20                  25                  30

Tyr Gln Ser Glu Val Asp Ile Tyr Asn Arg Ile Arg Asn Glu Leu
        35                  40                  45
```

<210> SEQ ID NO 19
<211> LENGTH: 47
<212> TYPE: PRT
<213> ORGANISM: Vibrio cholerae

<400> SEQUENCE: 19

```
Ser Met Ser Asn Thr Ser Asp Glu Lys Thr Gln Ser Leu Gly Val Lys
 1               5                  10                  15

Phe Leu Asp Glu Tyr Gln Ser Lys Val Lys Arg Gln Ile Phe Ser Gly
            20                  25                  30

Tyr Gln Ser Asp Ile Asp Thr His Asn Arg Ile Lys Asp Glu Leu
        35                  40                  45
```

<210> SEQ ID NO 20
<211> LENGTH: 131
<212> TYPE: PRT
<213> ORGANISM: Vibrio cholerae

<400> SEQUENCE: 20

```
Met Asn Lys Val Lys Phe Tyr Val Leu Phe Thr Ala Leu Leu Ser Ser
1               5                   10                  15

Leu Cys Ala His Gly Ala Pro Gly Tyr Ala His Gly Thr Pro Gln Asn
            20                  25                  30

Ile Thr Asp Leu Cys Ala Glu Tyr His Asn Thr Gln Ile His Thr Leu
        35                  40                  45

Asn Asp Lys Ile Phe Ser Tyr Thr Glu Ser Leu Ala Gly Lys Arg Glu
50                  55                  60

Met Ala Ile Ile Thr Phe Lys Asn Gly Ala Thr Phe Gln Val Glu Val
65                  70                  75                  80

Pro Gly Ser Gln His Ile Asp Ser Gln Lys Lys Ala Ile Glu Arg Met
                85                  90                  95

Lys Asp Thr Leu Arg Ile Ala Tyr Leu Thr Glu Ala Lys Val Glu Lys
            100                 105                 110

Leu Cys Val Trp Asn Asn Lys Thr Pro His Ala Ile Ala Ala Ile Ser
            115                 120                 125

Met Ala Asn
    130

<210> SEQ ID NO 21
<211> LENGTH: 103
<212> TYPE: PRT
<213> ORGANISM: Vibrio cholerae

<400> SEQUENCE: 21

Thr Pro Gln Asn Ile Thr Asp Leu Cys Ala Glu Tyr His Asn Thr Gln
1               5                   10                  15

Ile His Thr Leu Asn Asp Lys Ile Phe Ser Tyr Thr Glu Ser Leu Ala
            20                  25                  30

Gly Lys Arg Glu Met Ala Ile Ile Thr Phe Lys Asn Gly Ala Thr Phe
        35                  40                  45

Gln Val Glu Val Pro Gly Ser Gln His Ile Asp Ser Gln Lys Lys Ala
50                  55                  60

Ile Glu Arg Met Lys Asp Thr Leu Arg Ile Ala Tyr Leu Thr Glu Ala
65                  70                  75                  80

Lys Val Glu Lys Leu Cys Val Trp Asn Asn Lys Thr Pro His Ala Ile
                85                  90                  95

Ala Ala Ile Ser Met Ala Asn
            100

<210> SEQ ID NO 22
<211> LENGTH: 124
<212> TYPE: PRT
<213> ORGANISM: Escherichia coli

<400> SEQUENCE: 22

Met Asn Lys Val Lys Cys Tyr Val Leu Phe Thr Ala Leu Leu Ser Ser
1               5                   10                  15

Leu Cys Ala Tyr Gly Ala Pro Gln Ser Ile Thr Glu Leu Cys Ser Glu
            20                  25                  30

Tyr Arg Asn Thr Gln Ile Tyr Thr Ile Asn Asp Lys Ile Leu Ser Tyr
        35                  40                  45

Thr Glu Ser Met Ala Gly Lys Arg Glu Met Val Ile Ile Thr Phe Lys
50                  55                  60

Ser Gly Ala Thr Phe Gln Val Glu Val Pro Gly Ser Gln His Ile Asp
65                  70                  75                  80
```

```
Ser Gln Lys Lys Ala Ile Glu Arg Met Lys Asp Thr Leu Arg Ile Thr
                85                  90                  95

Tyr Leu Thr Glu Thr Lys Ile Asp Lys Leu Cys Val Trp Asn Asn Lys
            100                 105                 110

Thr Pro Asn Ser Ile Ala Ala Ile Ser Met Glu Asn
        115                 120
```

<210> SEQ ID NO 23
<211> LENGTH: 103
<212> TYPE: PRT
<213> ORGANISM: Escherichia coli

<400> SEQUENCE: 23

```
Ala Pro Gln Ser Ile Thr Glu Leu Cys Ser Glu Tyr Arg Asn Thr Gln
1               5                   10                  15

Ile Tyr Thr Ile Asn Asp Lys Ile Leu Ser Tyr Thr Glu Ser Met Ala
            20                  25                  30

Gly Lys Arg Glu Met Val Ile Ile Thr Phe Lys Ser Gly Ala Thr Phe
        35                  40                  45

Gln Val Glu Val Pro Gly Ser Gln His Ile Asp Ser Gln Lys Lys Ala
    50                  55                  60

Ile Glu Arg Met Lys Asp Thr Leu Arg Ile Thr Tyr Leu Thr Glu Thr
65                  70                  75                  80

Lys Ile Asp Lys Leu Cys Val Trp Asn Asn Lys Thr Pro Asn Ser Ile
                85                  90                  95

Ala Ala Ile Ser Met Glu Asn
            100
```

<210> SEQ ID NO 24
<211> LENGTH: 23
<212> TYPE: PRT
<213> ORGANISM: Escherichia coli

<400> SEQUENCE: 24

```
Met Ser Phe Lys Lys Ile Ile Lys Ala Phe Val Ile Met Ala Ala Leu
1               5                   10                  15

Val Ser Val Gln Ala His Ala
            20
```

<210> SEQ ID NO 25
<211> LENGTH: 6
<212> TYPE: PRT
<213> ORGANISM: Escherichia coli

<400> SEQUENCE: 25

```
Ser Thr Gly Asp Thr Cys
1               5
```

<210> SEQ ID NO 26
<211> LENGTH: 6
<212> TYPE: PRT
<213> ORGANISM: Escherichia coli

<400> SEQUENCE: 26

```
Ser Ile Gly Asp Thr Cys
1               5
```

<210> SEQ ID NO 27
<211> LENGTH: 22
<212> TYPE: PRT

-continued

<213> ORGANISM: Escherichia coli

<400> SEQUENCE: 27

Met Leu Lys Ile Lys Tyr Leu Leu Ile Gly Leu Ser Leu Ser Ala Met
1               5                   10                  15

Ser Ser Tyr Ser Leu Ala
            20

<210> SEQ ID NO 28
<211> LENGTH: 146
<212> TYPE: PRT
<213> ORGANISM: Escherichia coli

<400> SEQUENCE: 28

Ala Ala Gly Pro Thr Leu Thr Lys Glu Leu Ala Leu Asn Val Leu Ser
1               5                   10                  15

Pro Ala Ala Leu Asp Ala Thr Trp Ala Pro Gln Asp Asn Leu Thr Leu
            20                  25                  30

Ser Asn Thr Gly Val Ser Asn Thr Leu Val Gly Val Leu Thr Leu Ser
        35                  40                  45

Asn Thr Ser Ile Asp Thr Val Ser Ile Ala Ser Thr Asn Val Ser Asp
    50                  55                  60

Thr Ser Lys Asn Gly Thr Val Thr Phe Ala His Glu Thr Asn Asn Ser
65                  70                  75                  80

Ala Ser Phe Ala Thr Thr Ile Ser Thr Asp Asn Ala Asn Ile Thr Leu
                85                  90                  95

Asp Lys Asn Ala Gly Asn Thr Ile Val Lys Thr Thr Asn Gly Ser Gln
            100                 105                 110

Leu Pro Thr Asn Leu Pro Leu Lys Phe Ile Thr Glu Gly Asn Glu
        115                 120                 125

His Leu Val Ser Gly Asn Tyr Arg Ala Asn Ile Thr Ile Thr Ser Thr
    130                 135                 140

Ile Lys
145

<210> SEQ ID NO 29
<211> LENGTH: 16
<212> TYPE: PRT
<213> ORGANISM: Escherichia coli

<400> SEQUENCE: 29

Ala Ala Gly Pro Thr Leu Thr Lys Glu Leu Ala Leu Asn Val Leu Ser
1               5                   10                  15

<210> SEQ ID NO 30
<211> LENGTH: 166
<212> TYPE: PRT
<213> ORGANISM: Escherichia coli

<400> SEQUENCE: 30

Ala Ala Gly Pro Thr Leu Thr Lys Glu Leu Ala Leu Asn Val Leu Ser
1               5                   10                  15

Pro Ala Ala Leu Asp Ala Thr Trp Ala Pro Gln Asp Asn Leu Thr Leu
            20                  25                  30

Ser Asn Thr Gly Val Ser Asn Thr Leu Val Gly Val Leu Thr Leu Ser
        35                  40                  45

Asn Thr Ser Ile Asp Thr Val Ser Ile Ala Ser Thr Asn Val Ser Asp
    50                  55                  60

-continued

Thr Ser Lys Asn Gly Thr Val Thr Phe Ala His Glu Thr Asn Asn Ser
 65                  70                  75                  80

Ala Ser Phe Ala Thr Thr Ile Ser Thr Asp Asn Ala Asn Ile Thr Leu
                 85                  90                  95

Asp Lys Asn Ala Gly Asn Thr Ile Val Lys Thr Thr Asn Gly Ser Gln
            100                 105                 110

Leu Pro Thr Asn Leu Pro Leu Lys Phe Ile Thr Thr Glu Gly Asn Glu
        115                 120                 125

His Leu Val Ser Gly Asn Tyr Arg Ala Asn Ile Ile Thr Ser Thr
    130                 135                 140

Ile Lys Asp Asn Lys Gln Ala Ala Gly Pro Thr Leu Thr Lys Glu Leu
145                 150                 155                 160

Ala Leu Asn Val Leu Ser
                165

<210> SEQ ID NO 31
<211> LENGTH: 50
<212> TYPE: PRT
<213> ORGANISM: Escherichia coli

<400> SEQUENCE: 31

Ser Thr Val Ser Thr Gly Asp Thr Cys Asn Glu Glu Thr Gln Asn Leu
1               5                   10                  15

Ser Thr Ile Tyr Leu Arg Lys Tyr Gln Ser Lys Val Lys Arg Gln Ile
            20                  25                  30

Phe Ser Asp Tyr Gln Ser Glu Val Asp Ile Tyr Asn Arg Ile Arg Asn
        35                  40                  45

Glu Leu
    50

<210> SEQ ID NO 32
<211> LENGTH: 47
<212> TYPE: PRT
<213> ORGANISM: Escherichia coli

<400> SEQUENCE: 32

Ser Thr Gly Asp Thr Ser Asn Glu Glu Thr Gln Asn Leu Ser Thr Ile
1               5                   10                  15

Tyr Leu Arg Lys Tyr Gln Ser Lys Val Lys Arg Gln Ile Phe Ser Asp
            20                  25                  30

Tyr Gln Ser Glu Val Asp Ile Tyr Asn Arg Ile Arg Asn Glu Leu
        35                  40                  45

<210> SEQ ID NO 33
<211> LENGTH: 103
<212> TYPE: PRT
<213> ORGANISM: Vibrio cholerae

<400> SEQUENCE: 33

Thr Pro Gln Asn Ile Thr Asp Leu Cys Ala Glu Tyr His Asn Thr Gln
1               5                   10                  15

Ile Tyr Thr Leu Asn Asp Lys Ile Phe Ser Tyr Thr Glu Ser Leu Ala
            20                  25                  30

Gly Lys Arg Glu Met Ala Ile Ile Thr Phe Lys Asn Gly Ala Ile Phe
        35                  40                  45

Gln Val Glu Val Pro Gly Ser Gln His Ile Asp Ser Gln Lys Lys Ala
    50                  55                  60

Ile Glu Arg Met Lys Asp Thr Leu Arg Ile Ala Tyr Leu Thr Glu Ala

```
                65                    70                  75                   80
Lys Val Glu Lys Leu Cys Val Trp Asn Asn Lys Thr Pro His Ala Ile
                    85                  90                  95

Ala Ala Ile Ser Met Ala Asn
                100

<210> SEQ ID NO 34
<211> LENGTH: 25
<212> TYPE: PRT
<213> ORGANISM: Vibrio cholerae

<400> SEQUENCE: 34

Ser Ile Val Lys Arg Gln Ile Phe Ser Gly Tyr Gln Ser Asp Ile Asp
1               5                   10                  15

Thr His Asn Arg Ile Lys Asp Glu Leu
            20                  25

<210> SEQ ID NO 35
<211> LENGTH: 31
<212> TYPE: PRT
<213> ORGANISM: Escherichia coli

<400> SEQUENCE: 35

Ser Ile Glu Asn Tyr Gln Ser Lys Val Lys Arg Gln Ile Phe Ser Asp
1               5                   10                  15

Tyr Gln Ser Glu Val Asp Ile Tyr Asn Arg Ile Arg Asn Glu Leu
            20                  25                  30
```